US012806351B2

(12) United States Patent
Brady et al.

(10) Patent No.: US 12,806,351 B2
(45) **Date of Patent: *Nov. 24, 2026**

(54) INTUBATION ASSEMBLY TO PROTECT FROM AIRBORNE ILLNESSES

(71) Applicant: SafER Medical Products, LLC, Branson, MO (US)

(72) Inventors: Rob Brady, Sarasota, FL (US); Matt Vergin, St. Petersburg, FL (US); Barry Jennings, Largo, FL (US); Steve MacFarlane, Bradenton, FL (US); Richard Blubaugh, Branson West, MO (US); Craig Randall, Branson, MO (US); Misty Denevan, Branson, MO (US); Todd Baker, Walnut Shade, MO (US); Adriane Marie Jenkel, Bradenton, FL (US)

(73) Assignee: SafER Medical Products, LLC, Branson, MO (US)

( * ) Notice: Subject to any disclaimer, the term of this patent is extended or adjusted under 35 U.S.C. 154(b) by 1253 days.

This patent is subject to a terminal disclaimer.

(21) Appl. No.: 17/709,517

(22) Filed: Mar. 31, 2022

(65) Prior Publication Data

US 2022/0257887 A1 Aug. 18, 2022

Related U.S. Application Data

(63) Continuation-in-part of application No. 17/177,432, filed on Feb. 17, 2021, now Pat. No. 11,957,839.

(Continued)

(51) Int. Cl.

| | |
|---|---|
| ***A61M 16/00*** | (2006.01) |
| ***A61M 16/04*** | (2006.01) |
| ***A61M 16/10*** | (2006.01) |

(52) U.S. Cl.
CPC .... *A61M 16/0009* (2014.02); *A61M 16/0463* (2013.01); *A61M 16/1065* (2014.02)

(58) Field of Classification Search
CPC ....... A61M 16/00–0003; A61M 16/0087–009; A61M 16/04–0655; A61M 2016/0661; A61B 90/05
See application file for complete search history.

(56) References Cited

U.S. PATENT DOCUMENTS

| | | | |
|---|---|---|---|
| 3,136,515 | A | 6/1964 | Potruch |
| 4,794,921 | A | 1/1989 | Lindkvist |

(Continued)

FOREIGN PATENT DOCUMENTS

| | | | |
|---|---|---|---|
| CN | 105797246 | A | 7/2016 |
| CN | 206007759 | U | 3/2017 |

(Continued)

OTHER PUBLICATIONS

International Search Report and Written Opinion for PCT/US2021/049619; Feb. 28, 2022; ISA—United States Patent and Trademark Office; entire document.

(Continued)

*Primary Examiner* — Rachel T Sippel
(74) *Attorney, Agent, or Firm* — Ray Quinney & Nebeker P.C.; Joseph M. Evans

(57) ABSTRACT

An intubation assembly, shield assembly and related systems configured to at least partially reduce the risk of contagion from airborne illnesses. The shield assembly may be operatively connected to a vacuum system to exert a negative pressure and/or may be used as a standalone component as a barrier to reduce contamination of the local environment between therapies, treatments and/or procedures. The shield assembly may comprise ports to attach a vacuum device to provide negative pressure. An intubation (Continued)

apparatus assembly may be disposed on the shield assembly. The shield assembly comprises a body with a plurality of side segments and/or a transparent component(s) with a shield opening disposed thereon. The shield opening may be used for insertion of the intubation apparatus. The shield assembly may also comprise another transparent component with a longitudinally disposed slot(s) for insertion of an endotracheal tube or other intubation apparatus(es).

16 Claims, 22 Drawing Sheets

Related U.S. Application Data

(60) Provisional application No. 63/075,862, filed on Sep. 9, 2020.

(56) References Cited

U.S. PATENT DOCUMENTS

| | | | | |
|---|---|---|---|---|
| 4,807,617 | A | 2/1989 | Nesti | |
| 5,370,110 | A | 12/1994 | Corn | |
| 5,676,133 | A | 10/1997 | Hickle | |
| 7,647,928 | B2 | 1/2010 | Muellinger et al. | |
| 10,188,814 | B2 | 1/2019 | Moenning, Jr. | |
| 10,576,228 | B2 | 3/2020 | Blasdell et al. | |
| 11,049,626 | B1 | 6/2021 | Ahearn | |
| 12,083,273 | B1 | 9/2024 | Brady et al. | |
| 2002/0045796 | A1 | 4/2002 | O'Connor et al. | |
| 2003/0230678 | A1 | 12/2003 | Bellmore et al. | |
| 2009/0020128 | A1 | 1/2009 | Metzger et al. | |
| 2010/0229861 | A1 | 9/2010 | Nashed | |
| 2011/0144436 | A1 * | 6/2011 | Nearman | A61M 16/04 600/188 |
| 2014/0338677 | A1 | 11/2014 | Sparkuhl | |
| 2016/0074268 | A1 | 3/2016 | Breegi et al. | |
| 2016/0107006 | A1 | 4/2016 | Giulianotti et al. | |
| 2016/0136024 | A1 | 5/2016 | Poenisch et al. | |
| 2021/0307872 | A1 | 10/2021 | Vizulis et al. | |
| 2021/0346624 | A1 | 11/2021 | Fiorenza | |
| 2022/0015860 | A1 * | 1/2022 | Luk | A61B 90/40 |
| 2022/0355052 | A1 | 11/2022 | Alonso Babarro | |
| 2023/0142819 | A1 * | 5/2023 | Turer | A61B 90/05 600/21 |
| 2023/0147927 | A1 * | 5/2023 | Fisher | A61G 10/023 600/21 |

FOREIGN PATENT DOCUMENTS

| | | |
|---|---|---|
| WO | WO1995033506 | 12/1995 |
| WO | WO2021207292 | 10/2021 |

OTHER PUBLICATIONS

Sovereign Medical, Inc.; Exhlo Shield; Product Information Sheet; Online; Apr. 3, 2020; entire document; https://sovmed.com/wp-content/uploads/2020/07/EXHALO-Introduction-Summary-Soverign-Medical-ed3.pdf.

International Search Report and Written Opinion for PCT/US2021/048145; Dec. 9, 2021; ISA—United States Patent and Trademark Office; entire document.

Examination Report for Australian Patent Application No. 2021340655, mailed Jun. 10, 2026 (7 pp.).

* cited by examiner

INTUBATION ASSEMBLY TO PROTECT FROM AIRBORNE ILLNESSES

FIELD OF INVENTION

The present invention relates to protective shields for intubation, endoscope, bronchoscope, or other procedures that may generate aerosol or respiratory pathogens.

BACKGROUND

The spread of airborne illnesses poses a serious health risk, not only to individuals within the community, but also to health practitioners. This is relevant to patients that have contracted an airborne illness, for example a respiratory illness such as influenza, and more recently COVID-19. Such ill patients may require health practitioners to perform a procedure, for example an intubation, endoscopy, bronchoscopy, or other procedures, especially those requiring fiberoptic devices. During the process of performing the procedure, the health practitioners may be at risk of contagion of the airborne illness. Thus, a benefit would be realized by providing an intubation assembly that can act as a shield to cover the face of an ill patient. It would be ideal if such an intubation assembly would allow a health practitioner to insert a laryngoscope, endoscope, bronchoscope, or other fiberoptic device through the shield. Another benefit would also be realized if the intubation assembly would also allow the health practitioner to insert an endotracheal tube through the shield. An even further benefit would be realized if the shield comprised a substantially transparent material that would permit visibility of the patient and the intubation area. Yet a further benefit would be realized if such an intubation assembly would be provided with various operative components that would be capable of being connected to a vacuum system to provide for a negative pressure that may at least partially remove exhaled air from the patient. Another benefit would be realized if such a shield assembly would be provided as a standalone component that could be used on its own, not connected to a vacuum system, to protect other individuals and the environment from exhaled patient particles.

SUMMARY

The present invention relates to an intubation assembly and shield assembly that may at least partially reduce the risk of contagion of airborne illnesses, including from a patient to healthcare personnel, i.e., physician, nurse, assistant, etc. The present invention also relates to a method of using the inventive intubation assembly. The intubation assembly and shield assembly according to the present invention at least partially reduces exposure of healthcare personnel and others to exhaled infectious particles such as viruses and bacteria. The intubation assembly and shield assembly according to the present invention at least partially allows for protection against exhaled infectious particles. The shield assembly and/or intubation assembly according to the present invention should be capable of being used in connection with a vacuum system, which will be explained in more detail hereinafter. The inventive shield assembly and/or intubation assembly may also be used as "stand-alone" components. That is, the inventive shield assembly and/or intubation assembly may be used without being tied to a system that may provide an oxygen supply, air suctioning or nebulization, so that the shield assembly may protect the environment surrounding the patient from the spread of exhaled contaminated particles. Additionally, the shield body of the shield assembly may be secured to the head of the patient. As such, the shield body may follow or otherwise correspond to head movements of the patient while allowing for an optimal positioning of the patient for various procedures. The shield body should also follow or otherwise correspond to head movements while the patient is in a resting position, i.e., reclining, in a flat position, in a sitting position, etc. Such positioning of the shield body with respect to the head of the patient may allow the patient to continue to speak normally and communicate with others, e.g., clinical staff, while the shield body is disposed on the patient's head, including between treatments.

Further, the intubation assembly and shield assembly according to the present invention may at least partially provide a seal between the laryngoscope, endoscope, bronchoscope, or other fiberoptic device and the patient at the location where it is fitted and/or inserted. Furthermore, the intubation assembly and shield assembly according to the present invention may also at least partially provide a seal at the area where the endotracheal tube is inserted or otherwise passed through. Such a configuration of the intubation assembly and shield assembly, including in the geometry of a shield body, may substantially define an operable arrangement in conjunction with negative pressure vacuums. As such, the intubation assembly and shield assembly according to the present invention, when disposed in such operable arrangement, may at least partially remove the patient's exhaled air. This in turn, may protect the healthcare personnel involved in the procedure by at least partially reducing exposure to exhaled infectious particles.

Further embodiments of the present invention comprise a system configured to remove exhaled air from a patient in connection with an intubation or other related procedure. In such embodiments, it is contemplated that a portable vacuum unit be provided and connected to a vacuum tube that itself connects to the shield assembly, i.e., to the shield body, to create a negative pressure on an interior of the shield body and remove exhaled air. The innovative system may be provided with a shield body that may be placed around the face area of the patient to perform an intubation procedure through the mouth of the patient. Alternatively, the innovative system may be provided with a shield body that may be placed around the neck area of the patient to perform an intubation procedure around an opening on the neck area of the patient.

The intubation assembly comprises an intubation apparatus assembly and a shield assembly. The intubation apparatus assembly may be operatively disposed on a shield assembly. The shield assembly is generally connected to a negative pressure vacuum or otherwise vacuum system. The intubation apparatus assembly may comprise an intubation apparatus, including, but not necessarily limited to a laryngoscope, endoscope, bronchoscope, or other fiberoptic apparatus. The intubation apparatus may be placed on a correspondingly dimensioned sleeve of the intubation apparatus assembly. The sleeve should comprise a geometry such that a health practitioner should be able to hold it with a hand(s). The shield assembly comprises a body with a plurality of side segments. The shield assembly may also comprise a first transparent component with a shield opening disposed thereon. The shield opening may be used for insertion of the laryngoscope assembly. By way of example, the first transparent component may comprise a clear silicone sheet with an opening disposed thereon. The shield assembly may also comprise a second transparent component with at least one longitudinally disposed slot for insertion of an endotracheal tube, and in some embodiments, an endoscope, bronchoscope, or other fiberoptic apparatus.

DETAILED DESCRIPTION

Figure 11:
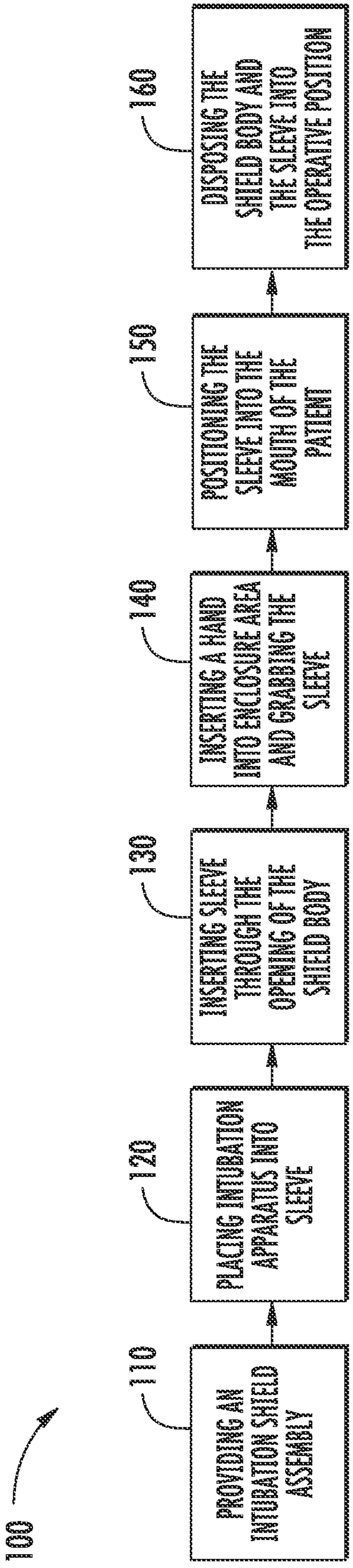
FIG. 11 is a diagrammatic representation of one embodiment of the method of using the intubation assembly according to the present invention.

With initial reference to at least FIGS. 1A-1D, the present invention relates to an intubation assembly, which is indicated at 1. With reference to at least FIG. 3, the present invention is also directed to a shield assembly 20. With reference to FIG. 11, the present invention is further directed to a method 100 of using the intubation assembly 1. It is within the scope of the present invention that the intubation assembly 1 and/or shield 20, using a negative pressure vacuum, at least partially reduce the risk of contagion of airborne illnesses, including from a patient to a health practitioner, i.e., physician, nurse, assistant, etc. That is, the intubation assembly 1 and/or shield 20 may act as a physical barrier that may at least partially reduce airborne movement of infectious particles, including but not necessarily limited to viruses, e.g., influenza or COVID-19, or bacteria, fungi, etc. The intubation assembly 1 and/or shield 20 may also at least partially reduce the risk of contagion of airborne illnesses from the health practitioner to the patient. The intubation assembly 1 generally comprises an intubation apparatus assembly 10 and a shield assembly 20. The intubation apparatus assembly 10 may be operatively disposed on a shield assembly 20. With reference to at least FIG. 2, it is within the scope of the present invention that the intubation assembly 1 and/or shield 20 be used with an intubation apparatus. As used herein, an "intubation apparatus" may include, without limitation, laryngoscopes, endoscopes, bronchoscopes, and other fiberoptic devices. As also used herein, an "intubation apparatus" may also refer to an endoscope assembly, or other related apparatus, as may be used, without limitation, in connection with an upper gastro intestinal (GI) endoscopy (EGD) or similar procedure. Furthermore, it is also contemplated that the inventive intubation assembly 1 be disposable. However, this is not strictly necessary as the inventive intubation assembly 1 may also be disinfected so that it may be used more than once.

Figure 2:
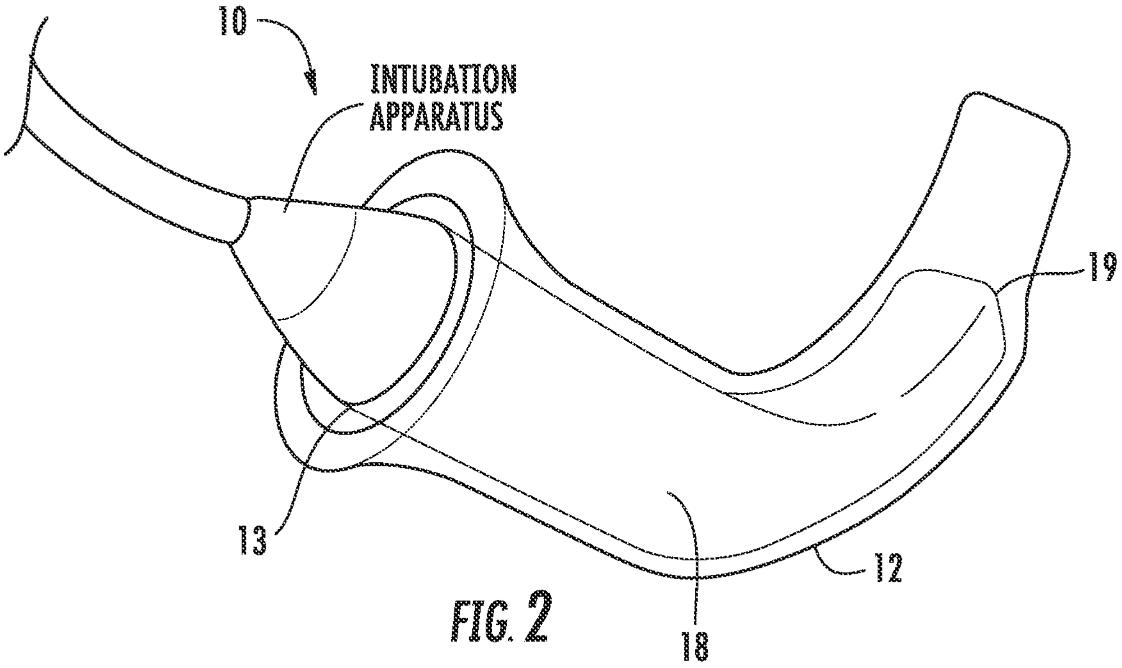
FIG. 2 is a perspective view of one embodiment of the laryngoscope assembly of the intubation assembly according to the present invention.

As is shown at least in FIG. 2, and as mentioned above, the inventive intubation assembly 1 comprises an intubation apparatus assembly 10. The intubation apparatus assembly 10 comprises an intubation apparatus, which may be disposed on a sleeve 12. The sleeve 12 is generally dimensioned to accommodate the size and/or length of the body 18 of the intubation apparatus. It is within the scope of the present invention that the sleeve 12 comprise a material that may create sufficient frictional resistance to engage the intubation apparatus once it is inserted inside of the sleeve 12. The sleeve 12 should also comprise a material that is sufficiently flexible may conform to the geometry of the intubation apparatus. It is also contemplated that the material of the sleeve 12 also permit a manual insertion of the intubation apparatus through a sleeve opening 13.

With reference to at least FIGS. 1B and 2, it is also contemplated that the size and geometry of the intubation apparatus assembly 10, including the intubation apparatus and/or sleeve 12, be configured and dimensioned to permit a health practitioner to hold it with a hand(s) after insertion onto the shield assembly 20, which will be described below. As shown at least in FIG. 1B, the sleeve 12 may comprise an elongated and/or curved profile. In the illustrative embodiment of FIG. 2, the sleeve 12 may comprise a substantially square opening, including with rounded corners. Alternatively, as shown at least in FIG. 2 the sleeve 12 may comprise a substantially circular opening 13 at one of its ends. With reference again to FIG. 1B, it is contemplated that the opening 13 of the sleeve 12 be sufficiently large to accommodate insertion of an intubation apparatus. Furthermore, in embodiments comprising a substantially rectangular opening, it is contemplated that the size and configuration of the shield opening 22 be configured and dimensioned accordingly to permit insertion of the sleeve 12 into the shield body 24. Similarly, in embodiments comprising a substantially cylindrical configuration, it is contemplated that the size of the opening 13 of the sleeve 12 comprise a diameter that is at least larger than the diameter of the shield opening 22, which will also be described in more detail below. Furthermore, the sleeve 12 may also comprise a tapered configuration, which may allow the health practitioner to insert it into the mouth, larynx, esophagus, and/or trachea of the patient. As is also appreciated in FIG. 2, the laryngoscope may also comprise an audiovisual component 19. For example, the audiovisual component 19 may comprise a camera.

Figure 3:
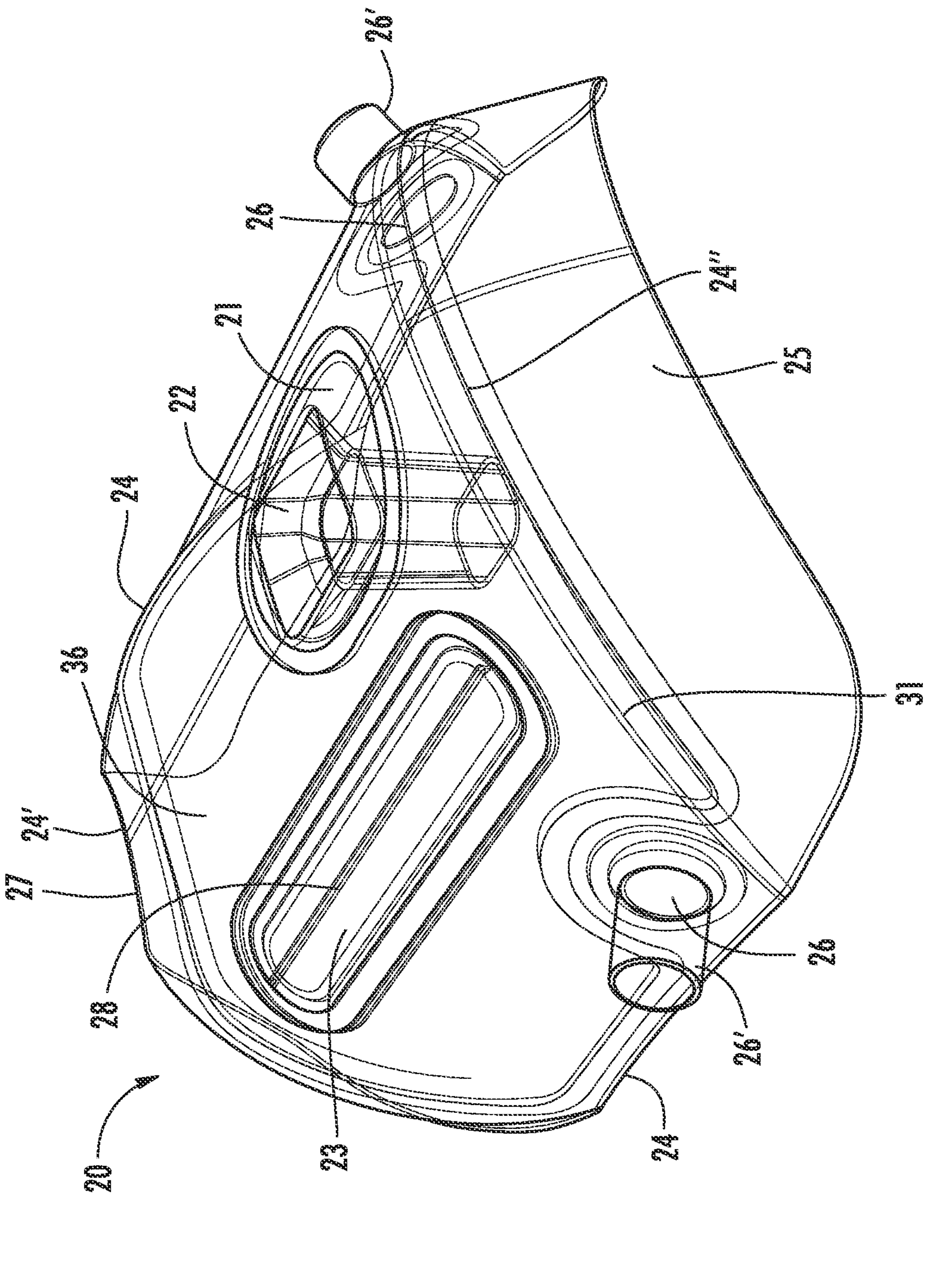
FIG. 3 is a perspective view of one embodiment of the shield assembly of the intubation assembly according to the present invention.

With reference now to at least FIG. 3, and as also referenced above, the present invention is directed towards an intubation assembly 1 comprising a shield assembly 20 as well as other embodiments comprising only the shield assembly 20. The shield assembly 20 comprises a body 24, which may comprise a plurality of side segments 29. The shield body 24 may comprise a top surface 36 and a bottom surface 37 as well as proximal end 24' and a distal end 24". The shield body may comprise a variety of shapes and/or configurations, including, without limitation, a substantially arched configuration as is shown throughout the figures. However, this is not necessarily limiting as other shapes and/or configurations are also possible. The shield body 24 may primarily comprise a substantially transparent or translucent material. For example, the body 24, including the side segments 29 may primarily comprise a clear plastic. The material of the body 24 may comprise a rigid clear plastic. The material of the side segments 29 may potentially comprise a flexible material that may allow for further positioning adjustments 29 of the shield body and/or which may at least partially reduce the risk of injury to the patient, as for example, with the flexible material of the top portion 25. The shield assembly 20 may comprise a first transparent component 21, which is disposed substantially around the middle of the body 24. The first transparent component 21 may comprise a substantially transparent or translucent material. Further, the first transparent component 21 may also comprise a shield opening 22 for insertion of the intubation apparatus assembly 10. By way of example, the first transparent component 21 may comprise a clear silicone sheet with an opening disposed thereon. The shield assembly 20 may also comprise a second transparent component 23. The second transparent component may comprise a slot(s) 28 and enabling a fluid communication between the area above the top surface 36 of the shield body 24 and the area below the bottom surface of the shield body 37. It is within the scope of the present invention that the slot(s) 28 remain substantially closed unless the health practitioner selectively opens them, for example to insert an endotracheal tube, which will also be described in more detail later. As an example, the second transparent component 23 may comprise a clear silicone sheet a longitudinally disposed slot(s) 28.

Also with reference to at least the illustrative embodiment shown in FIG. 3, the shield assembly 20 of the intubation assembly 1 may comprise a top portion 25. The top portion 25 may be disposed on the distal end 24" of the shield body 24 and may comprise an elongated configuration. The top portion 25 may also comprise a substantially rounded or curved configuration. As shown at least in the illustrative embodiments of FIGS. 1A-1B and 3, the top portion 25 may be deposed at a downward inclination relative to the shield body 24. The top portion 25 may potentially comprise a flexible material to permit adjustments by the user and/or medical practitioner when positioning the shield body 24 on or around the patient, and/or to at least partially recue the risk of injury to the patient, for example to the neck or chest area of the patient. As such, the top portion 25 as well as the bottom surface 37 of the shield body 24 may substantially define an enclosure are 34, which is shown at least in FIG. 1D. The top portion 25 may also comprise a substantially soft or malleable material. For example, the top portion may comprise a soft silicone material. Furthermore, the top portion may comprise at least one vacuum opening 26. The vacuum opening 26 may be disposed in fluid communication with a vacuum connecting portion 26', which itself may be disposed in fluid communication with a vacuum tube. As such, a negative pressure may be transferred from the vacuum tube and/or system and exerted on the enclosure area 34. As shown in the illustrative embodiment of FIG. 3, two vacuum openings 26 may be provided. Further, a cap may be provided to cover one or both vacuum openings 26 and/or vacuum connecting portions 26". As an example, the vacuum openings 26 may comprise hose ports. The vacuum openings 26 may be operatively disposed with a vacuum system to provide negative pressure. As used herein, a “vacuum system” may refer to one or more components associated with vacuum equipment, including a vacuum tube or conduit that may exert a negative pressure, and/or other associated components, including, without limitation a vacuum machine and/or filtering apparatus. As such, and with reference to at least FIGS. 1A-1D and 3, one or more vacuum tubes may be operatively disposed on the vacuum openings 26 to enable a negative pressure on the side of the shield body 24 disposed against the face of the patient. As such, given the operative arrangement enabled by the geometry of the shield body 24 and vacuum openings 26, the resulting negative pressure should provide for an at least partially increased removal of exhaled infectious particles.

Figure 1A:
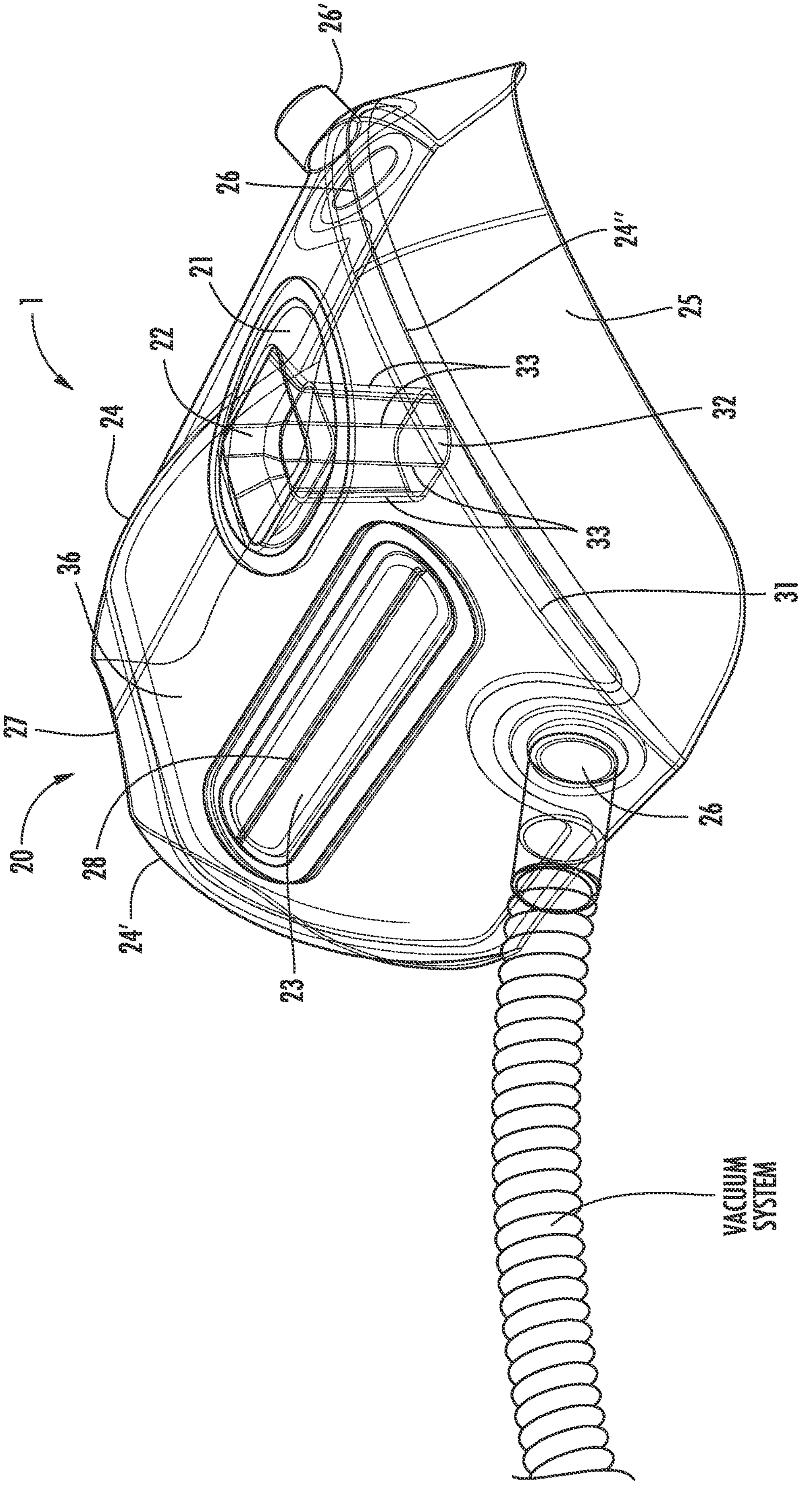
FIG. 1A is a perspective view of one embodiment of the intubation assembly according to the present invention.
Figure 1B:
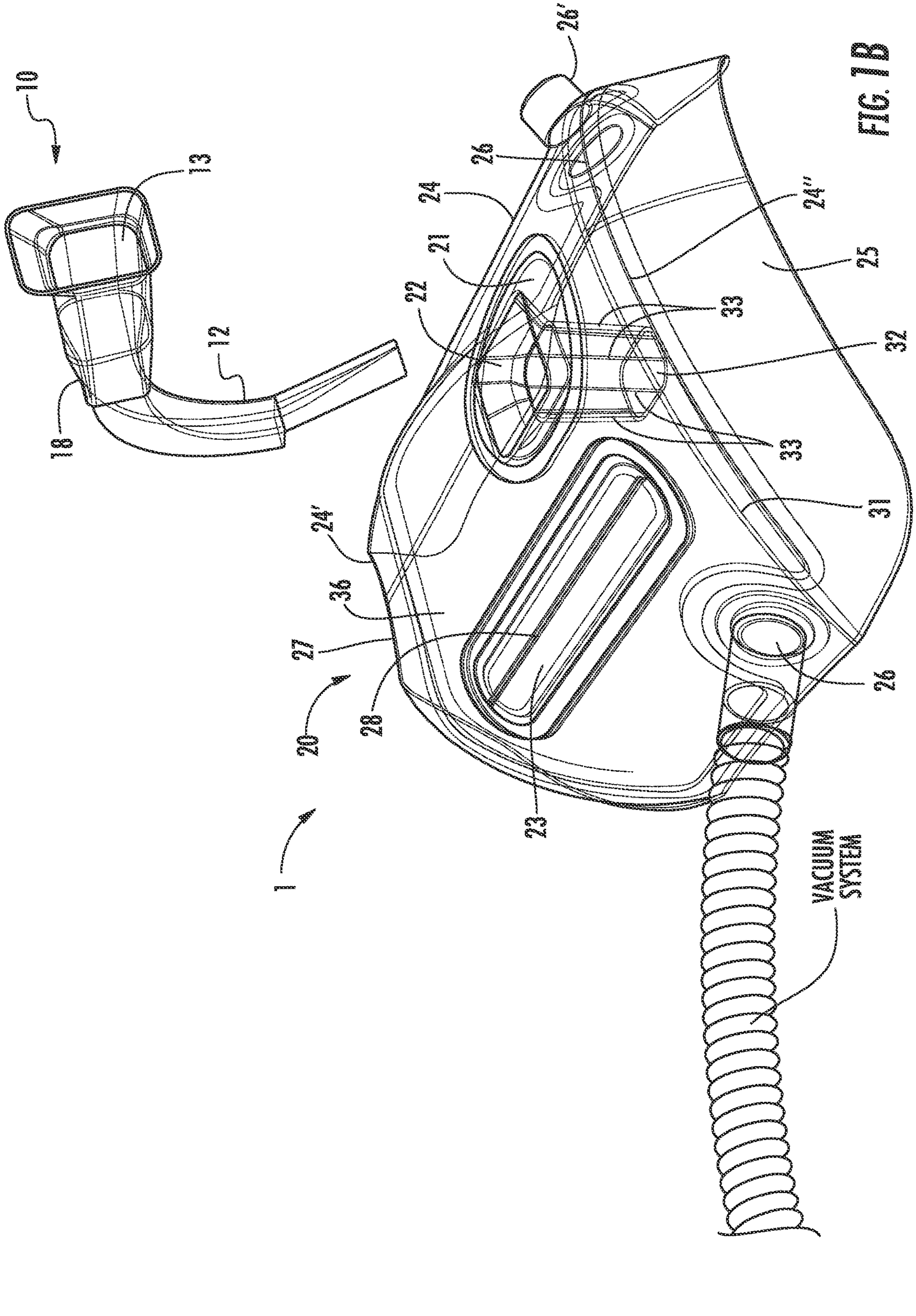
FIG. 1B is a perspective view of another embodiment of the intubation assembly according to the present invention.
Figure 1C:
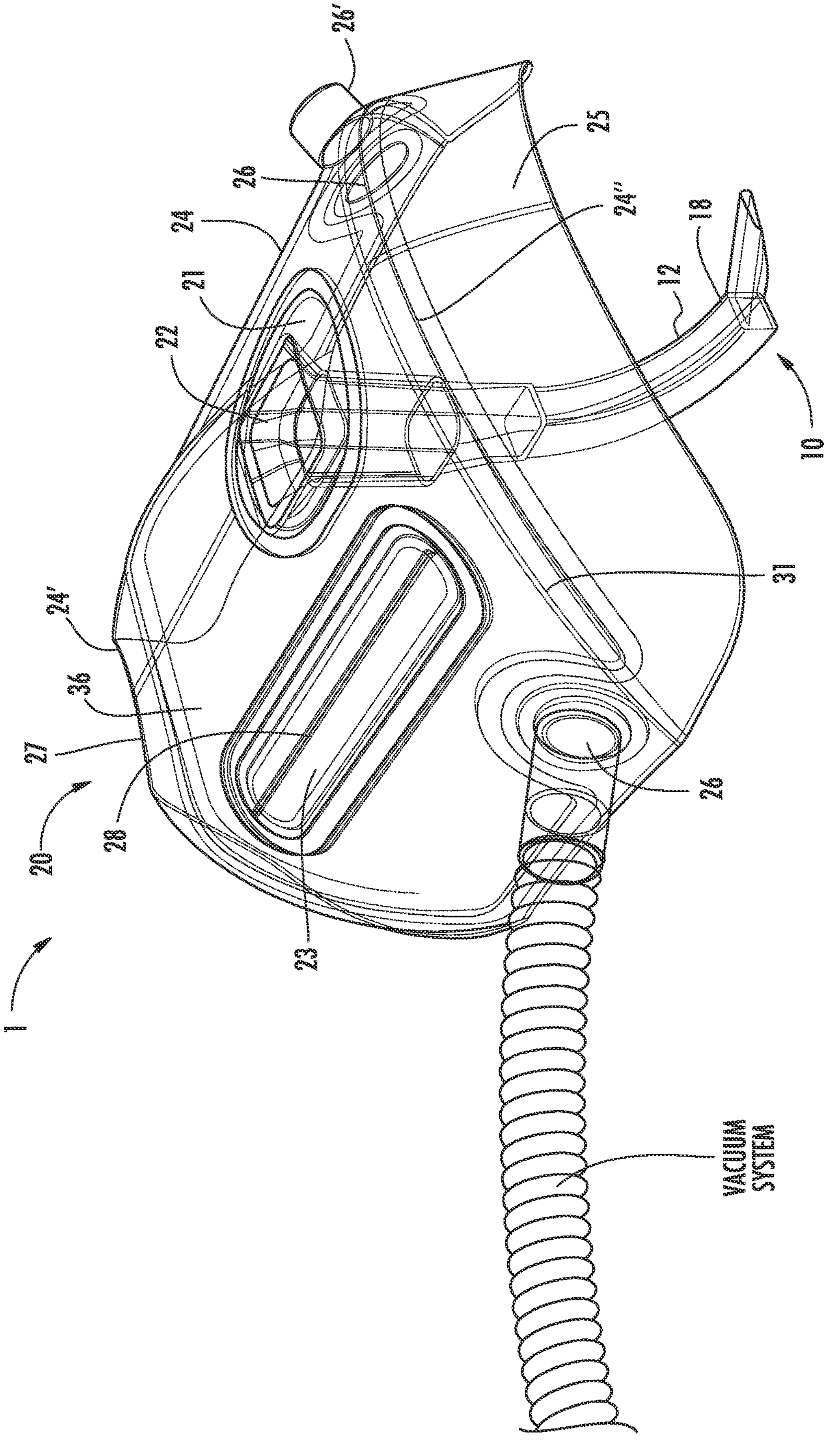
FIG. 1C is a perspective view of yet another embodiment of the intubation assembly according to the present invention.
Figure 1D:
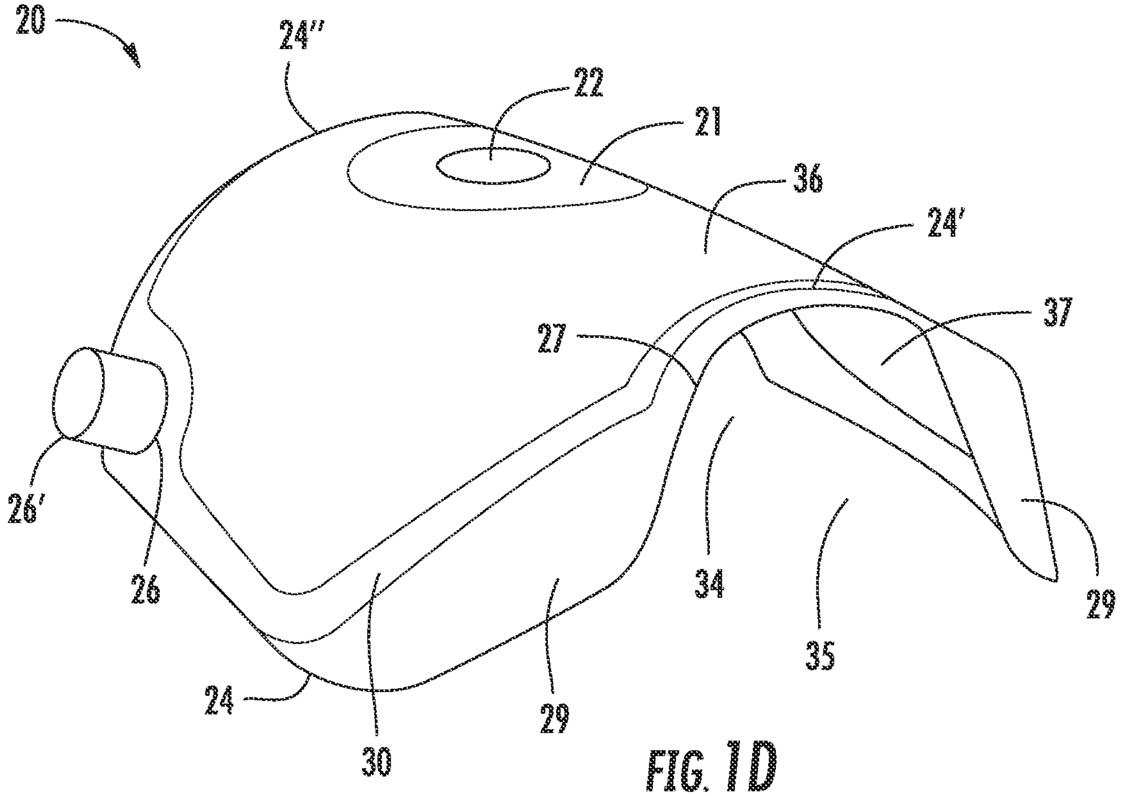
FIG. 1D is a perspective view of one embodiment of the shield assembly according to the present invention.

As is also shown at least in FIG. 1D, the shield assembly 20 may comprise a curvature 27. The curvature 27 may be substantially defined by the geometry of the ends of the side segments 29, which may for example comprise an elliptical configuration. The side segments 29 may be disposed on the proximal end 24' of the shield body 24, and further, may be disposed in a spaced apart relation to one another. As shown at least in FIG. 1D, the spaced apart relation between the side segments 29 may at least partially define an aperture 35. As such, the curvature 27 of the body 24 is advantageous to accommodate the arm of a health practitioner when holding the intubation apparatus assembly 10. Further, it is within the scope of the present invention that the curvature 27, the side segments 29, and/or the shield body 24, be configured and dimensioned to define an aperture 35 of a geometry and/or a sufficient dimension that may allow a user or practitioner to place his/her hand through the aperture 35 and into the enclosure area 34. As such, the user or practitioner may grab a sleeve 12 that has been inserted into the shield body 24.

Figure 4:
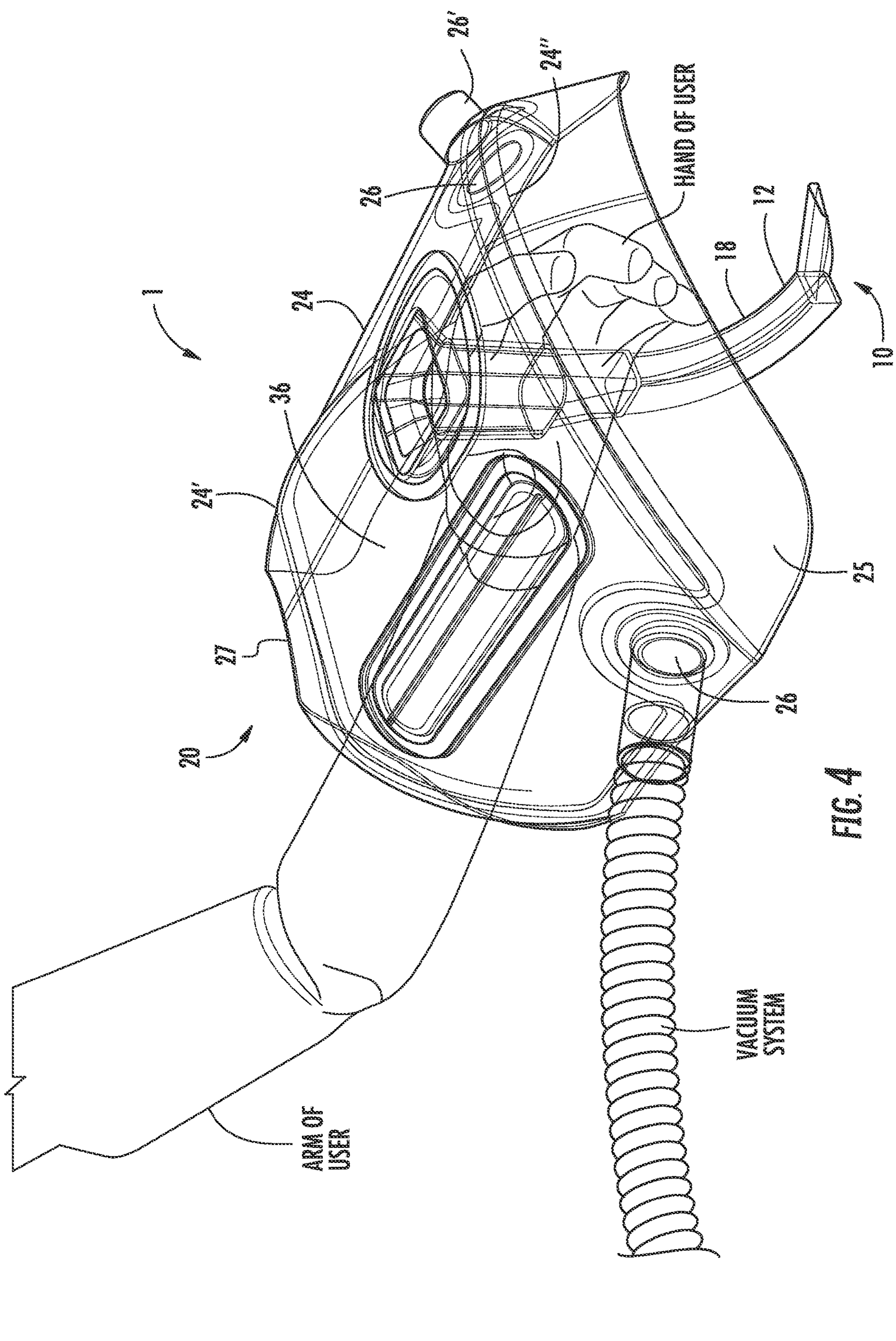
FIG. 4 is a perspective view of another embodiment of the shield assembly of the intubation assembly according to the present invention being operated by a user.

With reference now to FIGS. 1B and 4, and as mentioned above, it is within the scope of the present invention that the intubation apparatus assembly 10 be inserted into the sleeve opening 13 of the shield body 24. As such, a health practitioner may grab and/or position the intubation apparatus assembly 10 on an intended area of the body of the patient, e.g., the mouth, larynx, esophagus, and/or trachea. Because the diameter of the substantially circular configuration 13 of the sleeve 12 should be at least larger than the diameter of the shield opening 22, the sleeve 12 should be retained around its end on the first transparent component 22. However, the sleeve 12 should protrude on an opposite side of the shield body 24, i.e., the side facing the patient. As is perhaps best shown in FIG. 4, the sleeve 12 should remain movable with respect to the shield body 24 after insertion. However, the sleeve 12 should substantially pass through shield opening 22.

As is perhaps best shown in the illustrative embodiment of FIG. 3, the shield body 24 may comprise a sleeve retainer 32 disposed on the bottom surface 37. The sleeve retainer 32 is intended to act as a guide and/or support to the sleeve 12 once it has been inserted into the shield body 24. Accordingly the sleeve retainer 32 may be a channel or conduit which may extend below the shield opening 22 in a direction that is substantially perpendicular to the bottom surface 37. The sleeve retainer 32 should comprise an opening that corresponds to the shape of the shield opening 22 and/or sleeve 12, e.g., substantially square or substantially circular. The sleeve retainer 32 should allow for movement and/or adjustment of an inserted sleeve 12. For example, sleeve retainer 32 may be provided with four adjacently disposed walls to form a substantially square configuration extending away from the bottom surface 37. The sleeve retainer 32 may be provided with a recessed wall(s). That is, at least one of the adjacently disposed walls of the sleeve retainer 32 may comprise a lesser length that the other three to at least partially allow for movement and/or adjustment of the sleeve 12 in at least one direction. Additionally, an expandable component 33 may be provided along one or more of the walls to further allow for further movement and/or adjustment of the sleeve 12 in at least one direction, and in some embodiments in several directions. The expandable components 33 may comprise a corrugation or groove within the walls of the sleeve retainer 32, which may at least partially allow for such further movement and/or adjustment of the sleeve 12 once it has been inserted.

With reference now to at least FIGS. 1A-1D and 3, the shield assembly 20 may be provided with a reinforcement component 30 and/or an overlapping portion 31. A reinforcement component 30 and/or overlapping portion 31 may be provided to at least partially increase the stability of the shield body 24 and/or at least partially reduce bending of the shield body 24. As may be appreciated at least in FIG. 1D, the reinforcement component 30 may be disposed or otherwise formed on the top surface 36 of the shield body 24 around is proximal end 24'. The reinforcement component 30 may extend substantially along the width of the top surface 36 of the shield body. The reinforcement component 30 may comprise an elongated configuration and/or may follow or otherwise correspond to the profile of the curvature 27. The reinforcement component 30 may also be provided at an offset with respect to the curvature 27 and/or side segments 29. Conversely, and as may be appreciated at least in FIGS. 1A-1C and 3, the overlapping portion may be disposed or otherwise formed on the top surface 36 of the shield body 24 around its distal end 24". The overlapping portion 31 may be formed by an overlay or otherwise intersection between the shield body 24 and the top portion 25.

Figure 5:
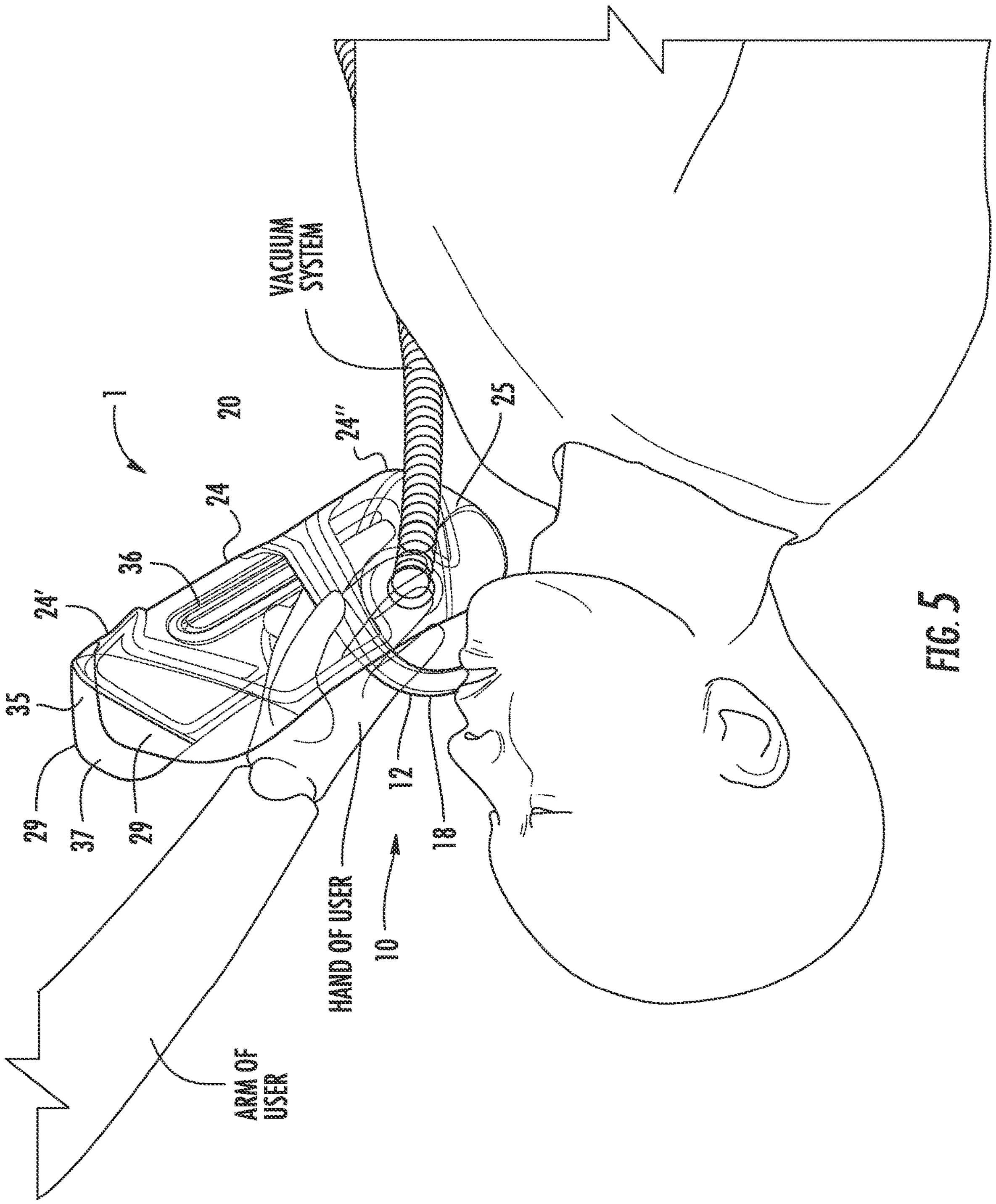
FIG. 5 is a side view of one embodiment of the shield assembly of the intubation assembly according to the present invention being operated by a user.
Figure 6:
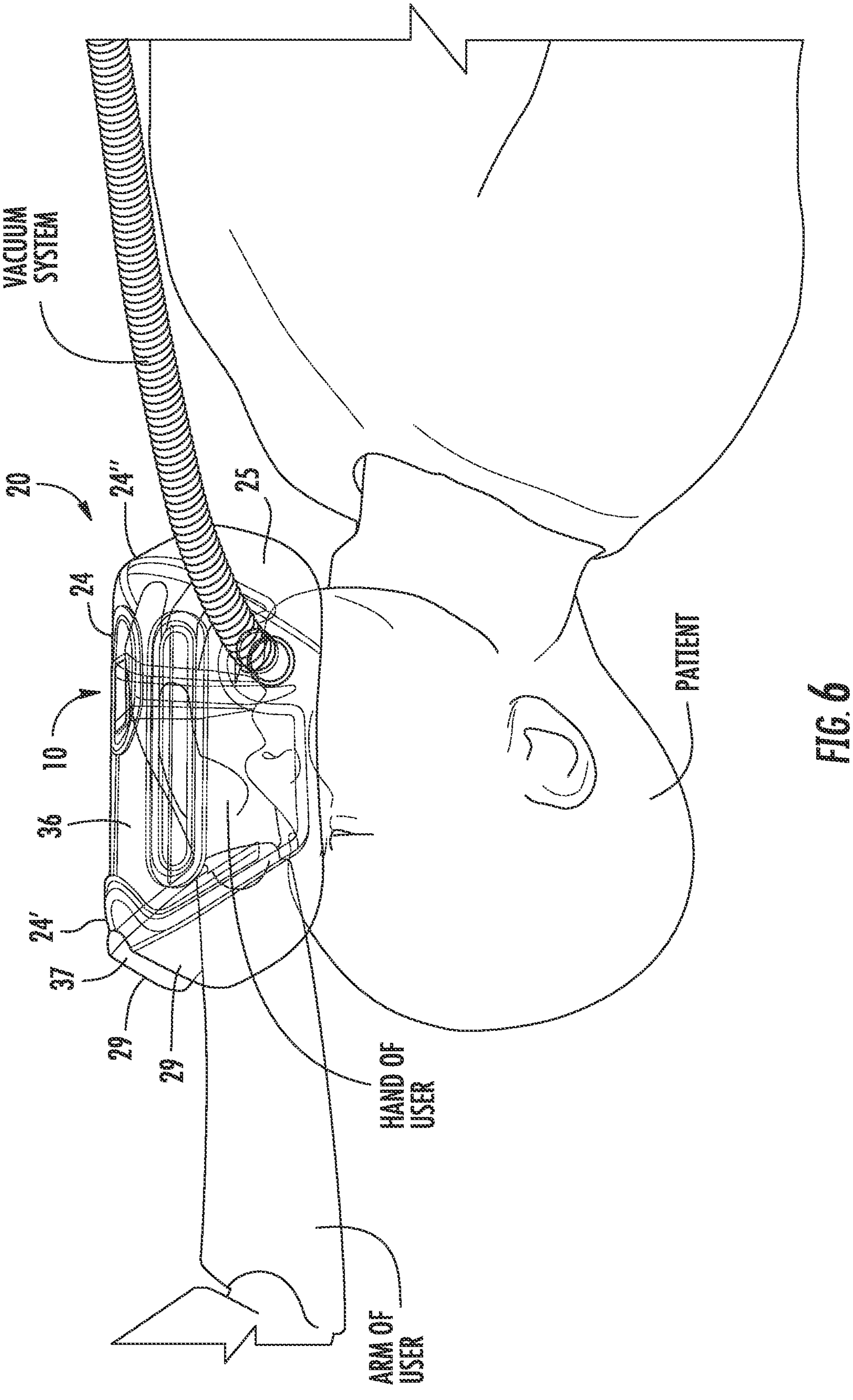
FIG. 6 is a side view of another embodiment of the shield assembly of the intubation assembly according to the present invention being operated by a user.

With reference now to FIGS. 4-8, features of the present invention comprise disposing the inventive intubation assembly 1 and/or shield assembly 20 into and out of an operative position and an inoperative position. As used herein, the "inoperative position" of the inventive intubation assembly 1 and/or shield assembly 20 refers the non-operation and/or storage of the various components of the intubation assembly 1 and/or shield assembly. The "inoperative position" may also refer to a position of the intubation assembly 1 and/or shield assembly 20 that does not involve placing the sleeve 12 into the shield body 24 or that does not involve dispose the shield assembly 20 in proximity to the face and/or head of the patient. Furthermore, the "inoperative position" may refer to the non-operation of a vacuum system connected to the shield assembly 20 and/or shield body 24. The "inoperative position" may also comprise periods where the shield body 24 is not used in connection with a vacuum system or with a sleeve 12, but is nonetheless disposed on the head of a patient and is used as a "barrier" to at least partially reduce travel or displacement of exhaled infectious particles, including between different procedures. With reference to FIG. 6, and as used herein, the "operative position" of the intubation assembly 1 and/or shield assembly generally comprises the intubation apparatus assembly 10, sleeve 12 and/or intubation apparatus, operatively disposed on the shield 24, i.e., inserted through the shield opening 22. The "operative position" also refers to the intubation apparatus assembly 10, sleeve 12 and/or intubation apparatus disposed the mouth, larynx, esophagus, and/or trachea of the patient, which for simplicity may be collectively referred to as the mouth of the patient. The "operative position" may also refer to the shield body 24 disposed in proximity to the patient, and/or the bottom surface 37 facing the patient. Furthermore, the "operative position" may comprise the vacuum system connected to the vacuum opening 26 and/or vacuum connecting portion 26', and being disposed in an operational setting, i.e., exerting a negative pressure, such that a negative pressure is transferred to the enclosure area 34 and/or the area surrounding the patient. As such, at least partially exhaled air may be extracted from the area surrounding the patient, while the user or practitioner performs an intubation procedure.

Figure 7:
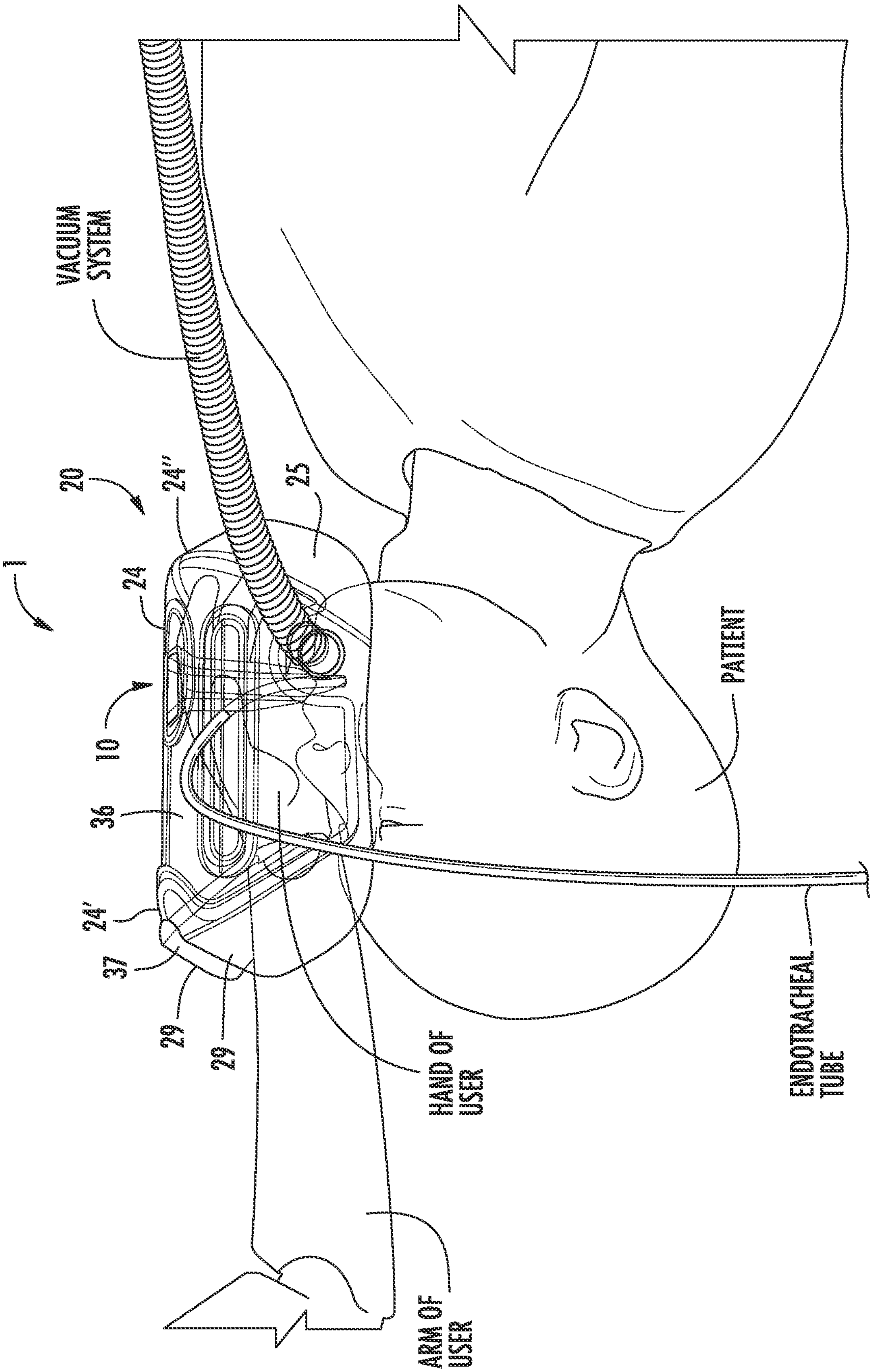
FIG. 7 is a side view of yet another embodiment of the shield assembly of the intubation assembly according to the present invention being operated by a user.
Figure 8:
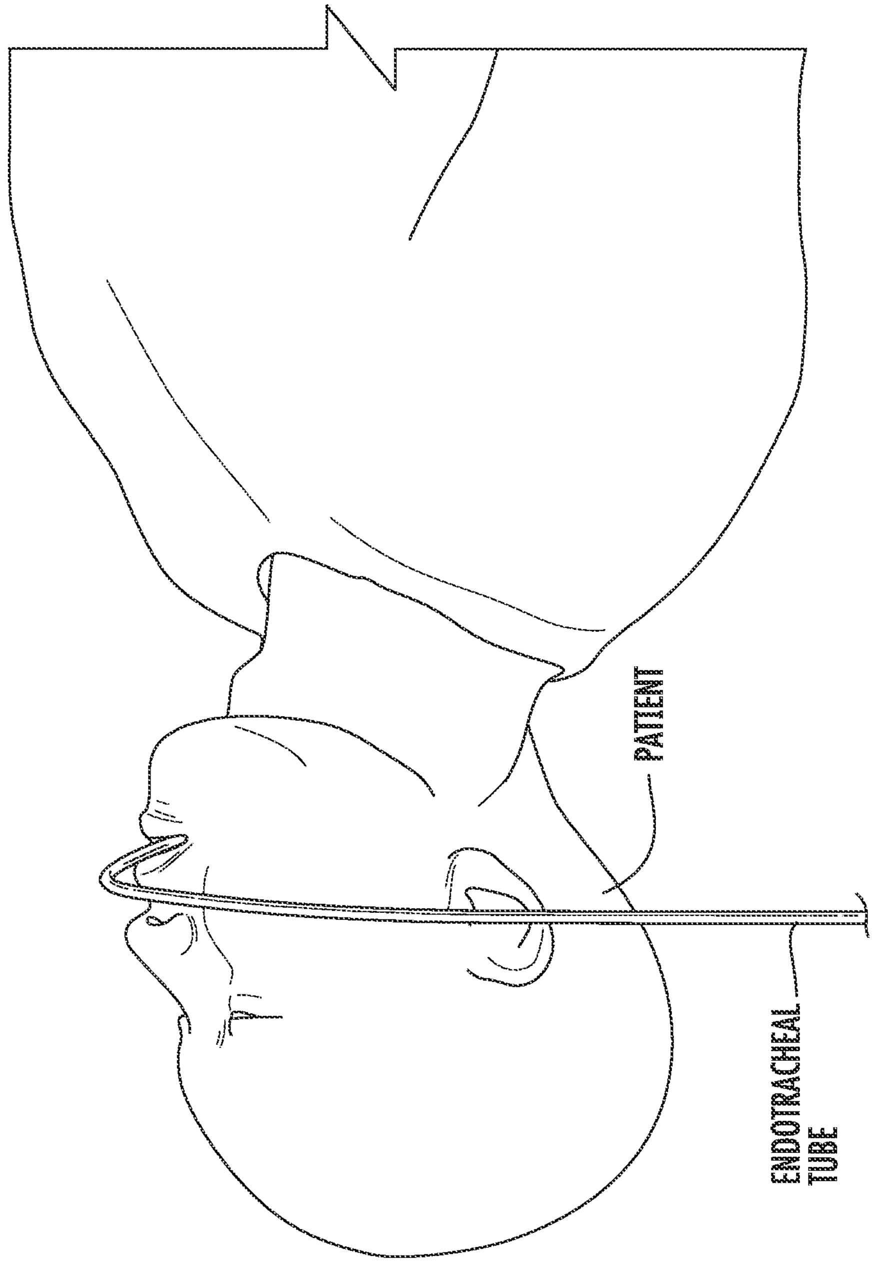
FIG. 8 is a side view of a patient intubated with the intubation assembly removed.

As shown in FIG. 5, the shield assembly 20, with the intubation apparatus assembly 10 and/or sleeve 12 inserted, may be positioned at a slight inclination with respect to the body of the patient. This at least partially facilitates an initial insertion of the sleeve 12 into the mouth of the patient. Here, the top portion 25 of the shield assembly 20 may come into contact with the neck of the patient. Accordingly, it is advantageous to provide a top portion 25 with a substantially soft material, e.g., soft silicone, to at least partially reduce the risk of physically injury, including around the neck of the patient. Once the sleeve 12 is initially inserted into the mouth of the patient, the shield assembly 20 may be manually moved from the position represented in FIG. 5 to the position represented in FIG. 6. During this process, the sleeve 12 may be inserted deeper into the mouth, and into the larynx, esophagus, and/or trachea of the patient. As shown in FIG. 7, once the shield assembly 20 and/or the intubation apparatus assembly 10 are disposed in an operative position, i.e., the position as represented in FIG. 6, an endotracheal tube may be passed through a slot 28 from an outside of the shield body 24 to the opposite side facing the patient. After being inserted through the at least one of the slots 28, the endotracheal tube may be placed on mouth of the patient. Thereafter, the endotracheal tube may be selectively positioned on an intended area of the patient, for example, an intended location of the larynx and/or trachea. At this stage, the audiovisual component 19 may assist the health practitioner in positioning the endotracheal tube on the intended area of the patient. As shown in FIG. 8, after the endotracheal tube has been inserted and/or positioned on an intended area of the patient, the shield assembly 20 and intubation apparatus assembly 10 may be removed.

Figure 9:
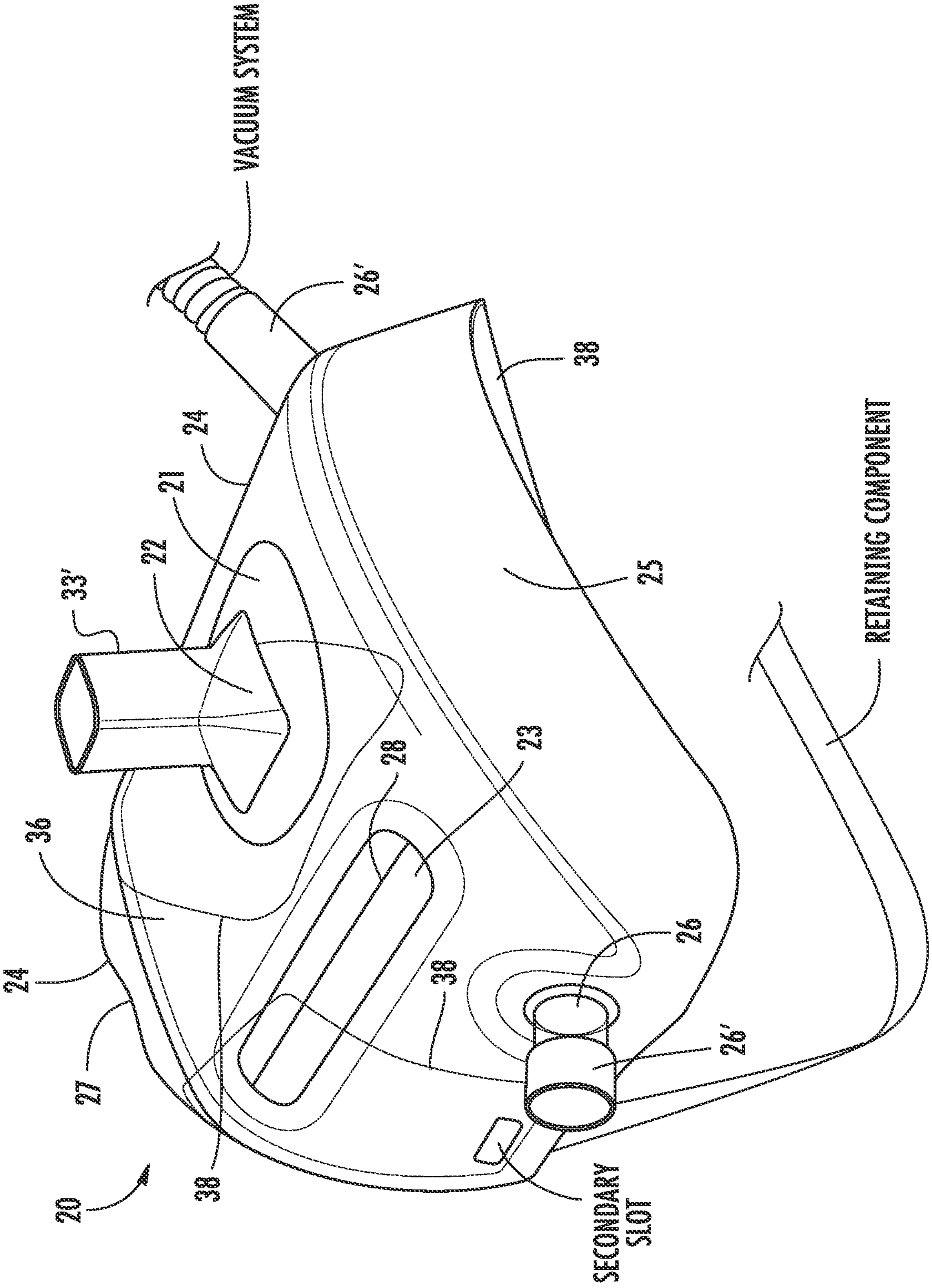
FIG. 9 is a perspective view of one embodiment of the shield assembly of the intubation assembly according to the present invention comprising offset structures.
Figure 10:
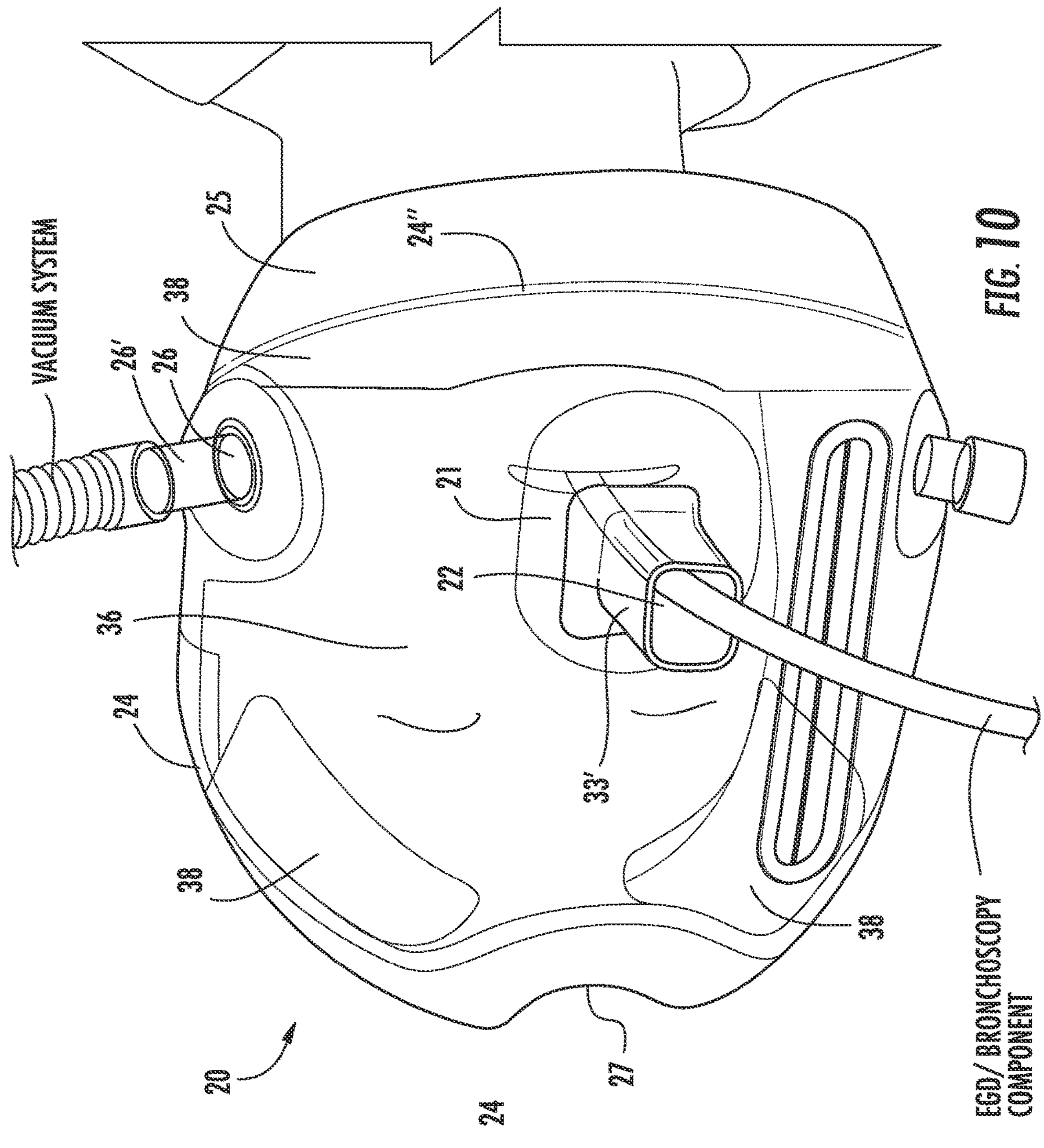
FIG. 10 is a front view of one embodiment of the shield assembly of the intubation assembly according to the present invention comprising offset structures and being operatively disposed on the head of a patient.

With reference to FIGS. 9-10, additional features of the present invention comprise providing a shield assembly 20 and/or an intubation assembly 1 with an offset structure 38. In some applications, it may be of interest that the shield body 24 be connected to the head of the patient, to at least partially limit movement of the shield 24 with respect to the body of the patient. For example, during an upper GI endoscopy (EGD) and/or a bronchoscopy, a retaining component, i.e., adjustable straps, ties, bands, etc., may be provided to dispose the shield body 24 around the head of the patient. The retaining component should at least partially reduce movement of the shield body 24 with respect to the body of the patient. The retaining component may be connected to the shield body around a secondary slot or opening configured and dimensioned for the size of the retaining component. For such applications, e.g., an upper GI endoscopy (EGD), a bronchoscopy and/or a related procedure, a shield body 20 may be provided with an offset structure 38, which is primarily intended to provide for a separation between the shield body 24 and the body of the patient, inducing the head, forehead, face, neck, upper portion of the chest, and/or shoulders, etc. It is within the scope of the present invention that such separation between the body and the offset structure 38 may be beneficial to at least partially protect the areas of the patient that may otherwise be in direct contact with the shield body 24, e.g., head, forehead, face, neck, upper portion of the chest, and/or shoulders. Accordingly, an offset structure 38 may be provided around the bottom surface 37 of the shield body 24.

As seen in FIGS. 9-10, the offset structure 38 may be provided around the bottom surface 37 of the shield body 24, including around the top portion 25 and/or the side segments 29. By way of example only, the offset structure 38 may comprise a foam pillow liner or other related material, e.g., a foam pad, such that it may serve to elevate or otherwise raise the position of the shield body 24 with respect to the body of the patient. As such, once the shield body 24 is disposed on the head of the patient, the intubation apparatus, e.g., bronchoscope and/or endoscope, may be inserted through the shield opening 22. In such embodiments, it is further contemplated that the vacuum opening(s) 26 and/or vacuum connecting portion(s) 26 also operate as described herein, to at least partially remove exhaled air from the patient with an operatively connected vacuum system. In such embodiments, and in addition to, or in lieu of, the offset structure(s) 38, a retainer 33' may be provided. The retainer 33' may be oriented outwards, i.e., away from the top surface 36, instead of inwards, i.e., away from the bottom surface 37 and/or towards the patient. A retainer 33' may be provided to further assist the user or practitioner to insert the intubation apparatus, e.g., EGD apparatus, bronchoscope and/or other related apparatus may be inserted through a retainer 33' disposed around the shield opening 22. As with the sleeve retainer 33, the retainer 33' is intended to function as a guide for the intubation apparatus.

With reference now to FIG. 11, the present invention is further directed to a method 100 of using the inventive intubation assembly 1. As shown at 110, the method 100 initially comprises providing an intubation assembly 1 comprising an intubation apparatus assembly 10 and a shield assembly 20 as described herein. As shown at 120, the method 100 further comprises placing an intubation apparatus into a sleeve 12 of the intubation apparatus assembly 10 of the inventive intubation assembly 1. As shown at 130, the method 100 further comprises inserting the sleeve 12 through the opening 22 of the shield body 24. As shown at 140, the method 100 further comprises inserting a hand of a user into the enclosure area 34 and grabbing the sleeve 12. As shown at 150, the method 100 further comprises positioning the sleeve 12 into the mouth of the patient. It should be understood that once the sleeve 12 is positioned into the mouth of the patient, that the shield body 24 will at least partially surround the face and/or head of the patient, and that the bottom surface 37 of the shield body 24 should face the patient. As shown at 160 the method 100 further comprises disposing the shield 24 assembly and the intubation apparatus assembly into the operative position.

With reference to FIGS. 12-18, further embodiments of the present invention relate to a system 1' configured to remove exhaled air from a patient. Generally, the system 1' according to the present invention is configured to remove exhaled air from a patient by placing a shield body 24 around the upper body area of the patient, i.e., neck and/or face area. With reference to at least FIGS. 12 and 13, the system 1' generally comprises a shield assembly 20 as defined herein, including a shield body 24 and/or 62, a vacuum tube 40 and a vacuum unit 80. As used herein, a vacuum unit 80 refers to a vacuum device, which may be motor operated, and which may be disposed in fluid communication with a vacuum tube 40, i.e., a hose, or other flexible or expandable hollow elongated component, and which may exert a negative pressure. It is contemplated that a shield body 24 of the shield assembly 20 also be disposed in fluid communication with the interior of the vacuum tube 40. The negative pressure of the vacuum unit 80 should be transferred through the vacuum tube 40, and to an interior face of the shield body 24, i.e., the area defined below bottom surface 37, the side of the shield body 24 that faces the patient and/or the enclosure area 34. As such, the shield body 24 essentially acts as a vacuuming device that is capable of at least partially removing exhaled air around the face of the patient. As used herein, the space defined by the interior face of the shield body 24 as well as the face of the patient, including when wearing the medical mask, is defined as an enclosure area 34.

Figure 13:
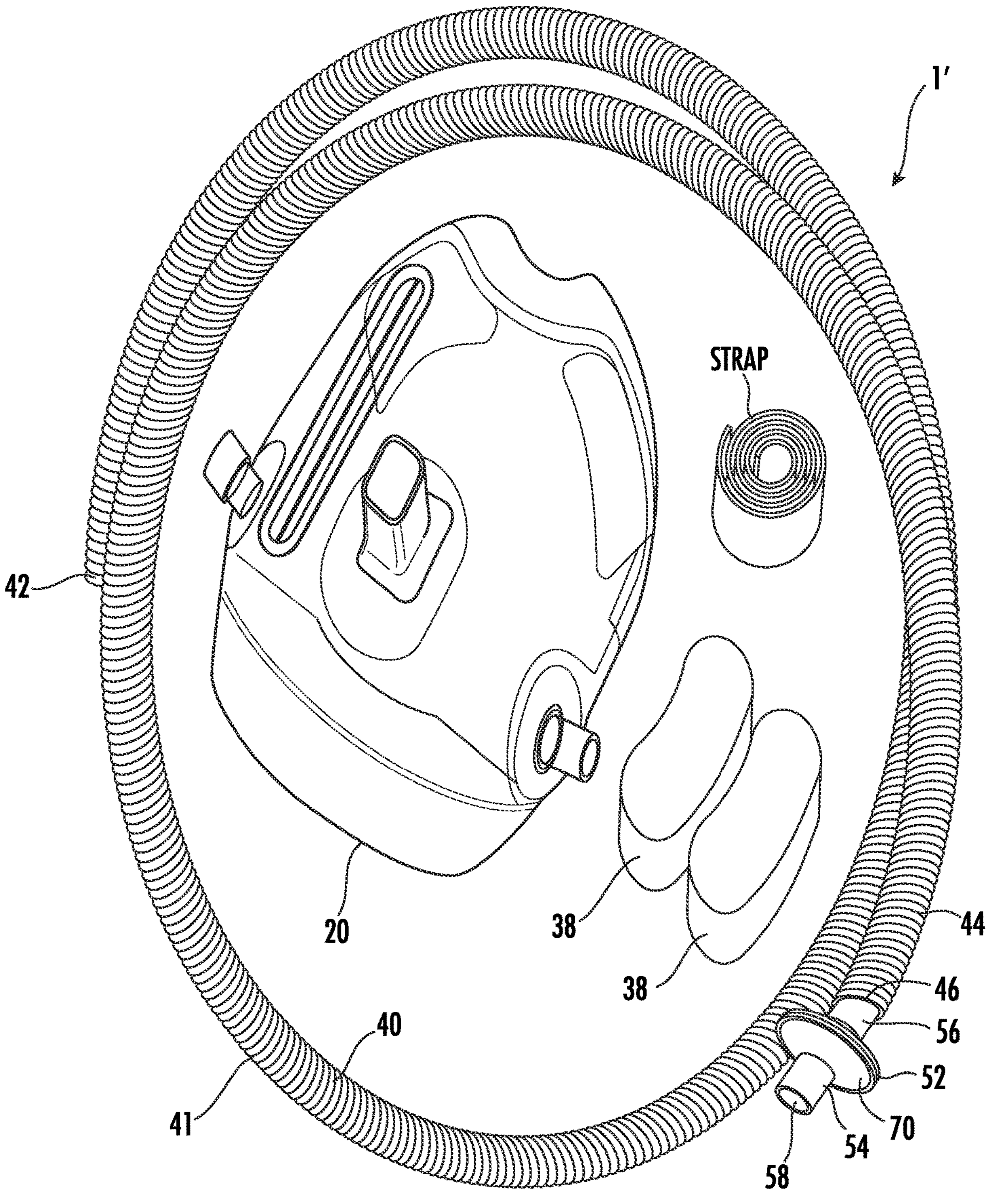
FIG. 13 is a perspective view of disassembled components of one embodiment of the system according to the present invention.

With reference to at least FIG. 13, the vacuum tube 40 may comprise a body 41 of a flexible, or elastic material that may at least partially bend, twist, move, or otherwise conform to geometric constraints. The vacuum tube 40 may comprise a proximal end 44 that connects to the vacuum unit 80 around connecting end 36, and a distal end 42 that connects to the shield body 24 around a connecting end 46. As is also shown at least in FIG. 13, the shield body 24 may also comprise a plurality of offset structures 38 which may assist in positioning the shield body 24 on the head of the patient. The offset structure(s) 38 are advantageous if the inventive shield body 24 is used as a standalone component as described herein. For example, the offset structure(s) 38 may be used to maintain its position relative to the head and/or face of the patient such that an intervening face mask or medical mask may not be required. As such, this provides a more comfortable fit of the shield body for certain patients. For example, a patient being administered oxygen via a cannula may not necessarily need a medical mask such that the shield body 24 may be disposed directly on the patient's head.

Figure 12:
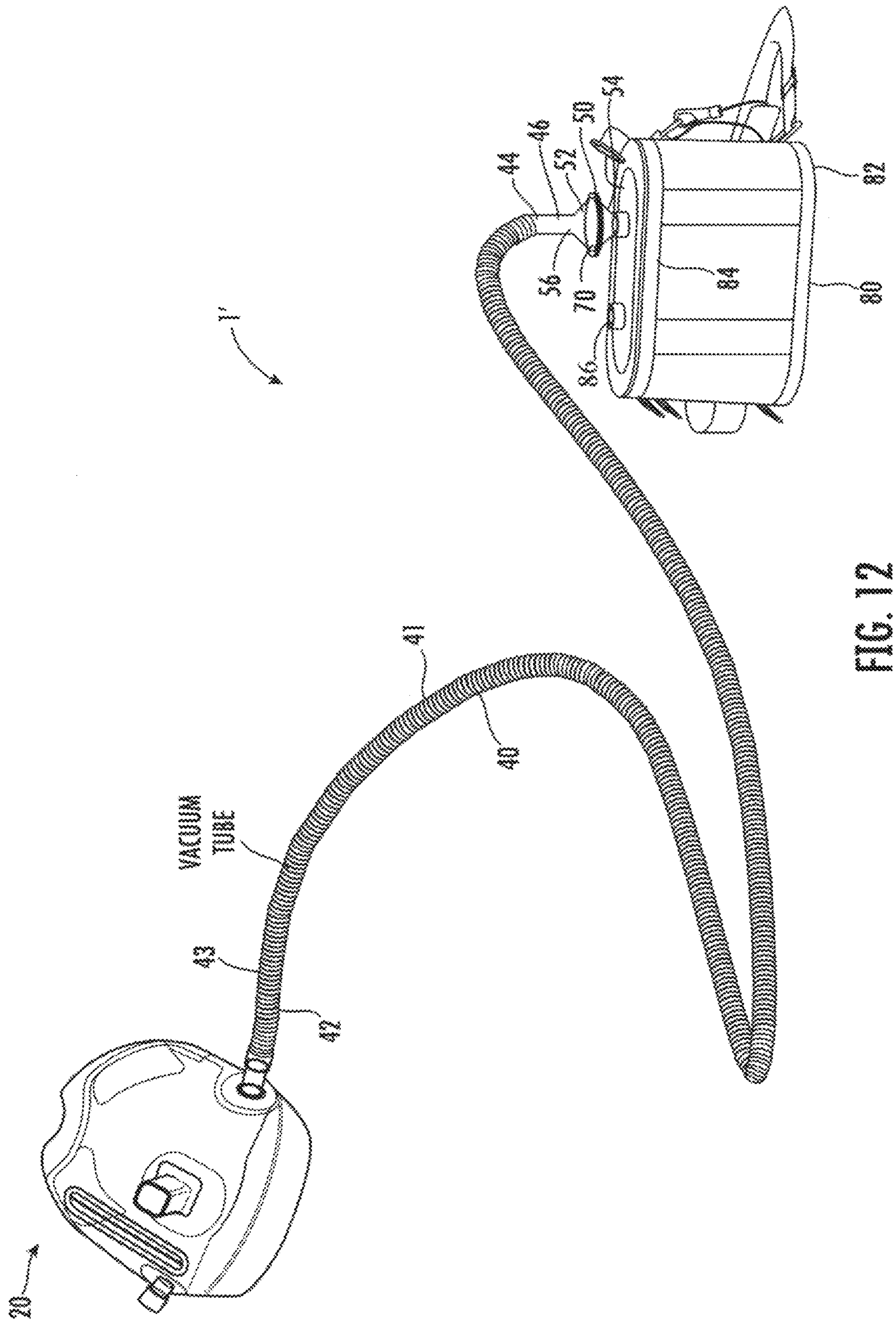
FIG. 12 is a perspective view of one embodiment of the system according to the present invention.

With reference to at least FIG. 12, a filter case assembly 50 may be disposed or integrally formed on the vacuum tube 40 around the proximal end 44. The filter case assembly 50 may comprise a top segment 52 and a bottom segment 54 which may be operatively connected to one another. In other words, the top segment 52 and bottom segment 54 may form a mating engagement with one another in a secured position, i.e., once a filter 70 has been placed between them. It is contemplated that the mating engagement between top segment 52 and bottom segment 54 not be a permanent mating engagement such that the top segment 52 and bottom segment 54 may removably connected to another to insert and/or remove a filter in the area where they engage. The diameters of the top segment 52 and/or bottom segment 54 should correspond to one another and should be configured and dimensioned to accommodate the diameter and/or size of a filter 70, which may comprise an air filter such as an ultra-low particulate air (ULPA) filter. The filter 70 may also comprise a high efficiency particulate air (HEPA) filter. As such, the diameters of the top segment 52 and/or bottom segment 54 may be larger than the diameter of the vacuum tube 40, but this is not strictly necessary. When the top segment 52 and the bottom segment 54 are forming a mating engaged, this should restrict placement or otherwise movement of a filter 70 disposed therein. Furthermore, the top segment 52 and/or upper segment 54 may be provided with conical or semi-conical shapes. This may be done to at least partially facilitate airflow through the vacuum tube 40 and into the vacuum unit 80 and/or to otherwise at least partially reduce the likelihood of a bottleneck effect around the area where the filter 70 is disposed. Consequently, air captured around a distal end 42 of the vacuum tube will pass through the filter 70 before entering the vacuum unit 80, at least partially reducing contaminants and/or other infectious particles.

With reference to at least FIG. 12, and as mentioned above, the system 1' according to the present invention comprises a vacuum unit 80. The vacuum unit 80 should provide for a portable solution of creating a negative vacuum pressure, at least around its first opening 84 where the vacuum tube 40 will be connected. The vacuum unit 80 may comprise a housing 82 with a first opening 84 and a second opening 86. The first opening 84 is generally configured for attachment of the vacuum tube 40, for example, around a proximal end 44 thereof. The second opening 86 is generally configured for captured air to exit outside of the housing 82. That is, air collected form the enclosure area 34 that passes through the first opening 84 and into the interior of the housing 82, should be able to exit outside of the housing 82 through the second opening 86. Alternatively, other means of air escape may be provided on the housing, and may include slots or vents, including disposed on the sides. In addition, the interior of the housing 82, which is generally a chamber, may be provided with other filtering means to further remove contaminants and/or infections particles form the air captured around the enclosure area 34. Also, a top cover of the housing may be removable from the rest of the housing 82 to access any components thereof, which may include a battery-operated vacuum with a motor, additional filtering components, etc. By way of example only, a battery-operated vacuum motor of 110V or similar, may be provided on an inside of the housing 82. This, however, is not limiting as motors configured for operation with other voltages may be provided, including 220V or other power supply configurations.

Specific to the system 1' according to the present invention, the vacuum unit 80, vacuum tube 40 and shield body 24 may be collectively disposable into and out of an operative orientation and an inoperative orientation. The operative orientation comprises the vacuum unit 80 activated and exerting a negative pressure on an inside of the shield body 24, i.e., around the enclosure area 34, to at least partially remove exhaled patient air. The inoperative operation comprises periods of non-operation of the system 1', including when the vacuum unit 80 is inactive. It is contemplated that the shield body 24 may be disposed into and out of an operative position, as shown at least in FIGS. 16B and 14E. The operative position generally comprises an intubation apparatus disposed on the shield opening 22 and into the mouth of the patient. The operative positon may also comprise the interior of the shield body 24, i.e., the bottom surface 37, facing the patient. Alternatively, and with reference again to at least FIG. 18, the operative position may comprise an intubation apparatus disposed into the opening 68 of a shield body 62 and into the trachea of the patient through a neck opening, with the interior or inner surface' of the shield body 62 disposed against the neck of the patient. In the operative orientation, the shield body is disposed into the operative position and the vacuum unit 80 is activated to exert a negative pressure on an inside of the shield body, or otherwise the enclosure area 34, at least partially removing exhaled air from the patient.

Figure 16:
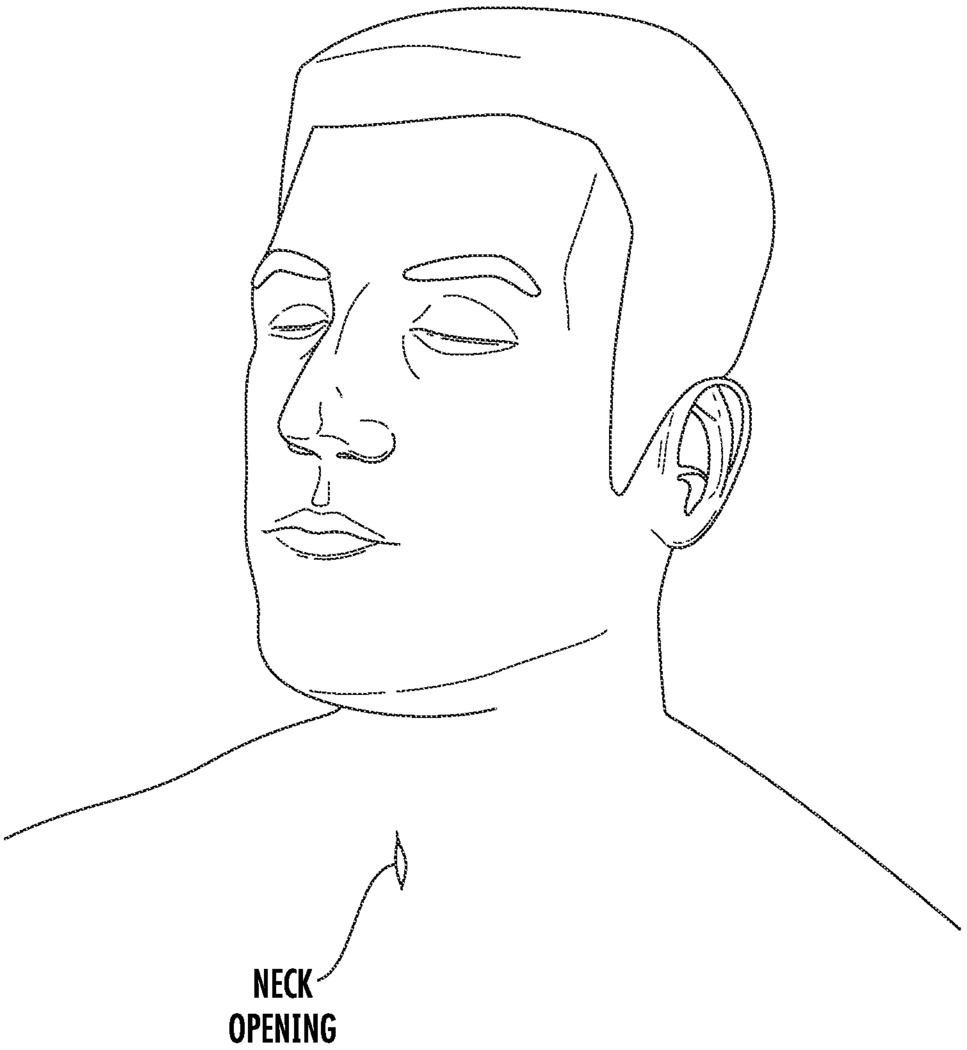
FIG. 16 is a perspective view of a patient with an opening around the neck area.
Figure 16A:
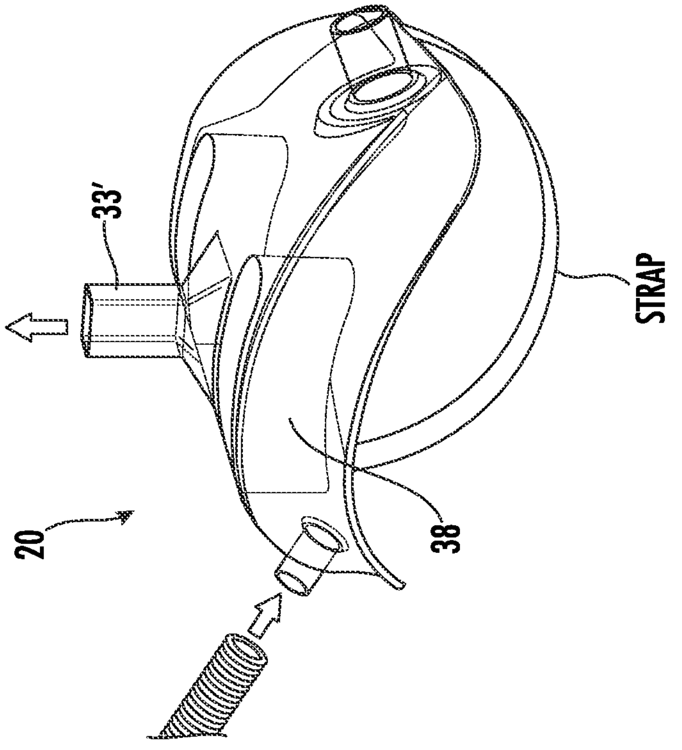
FIG. 16A is a perspective view of one embodiment of the shield body of the system according to the present invention.
Figure 17:
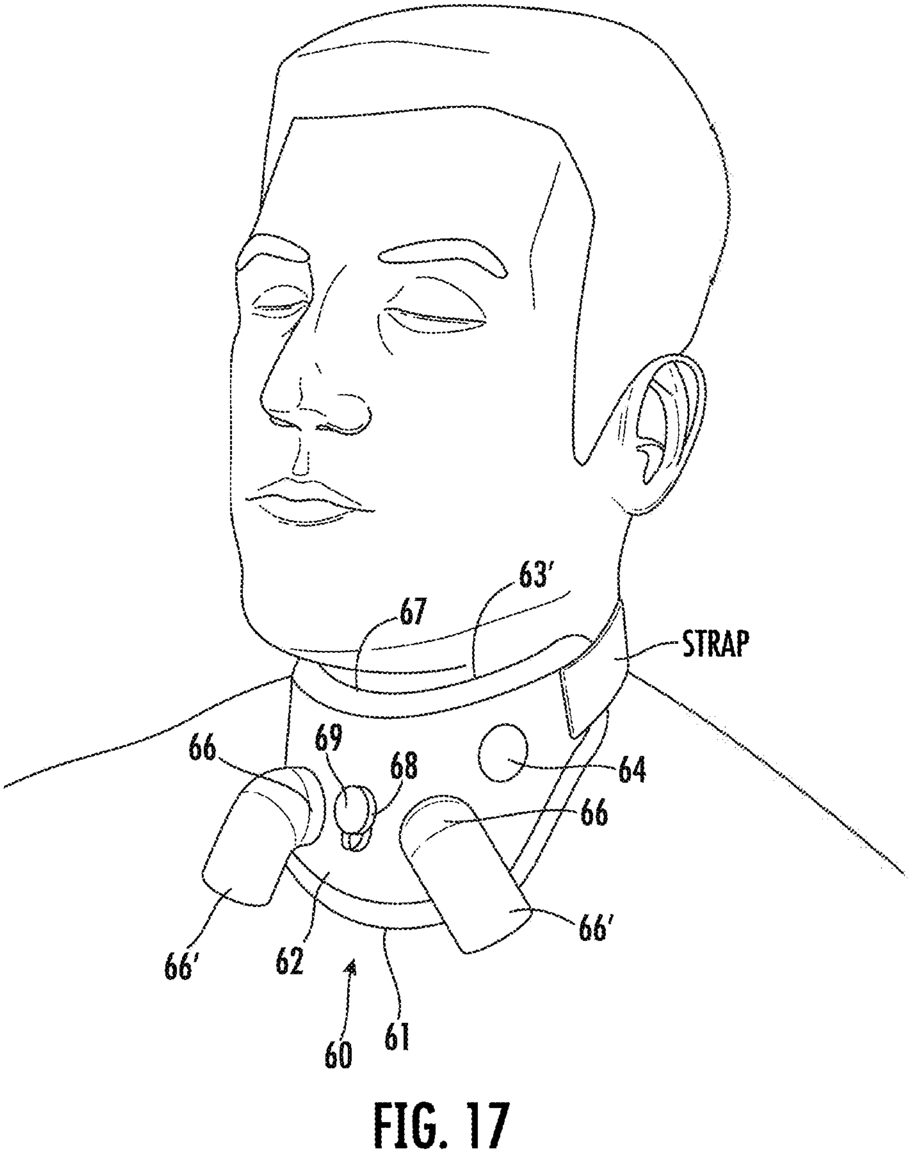
FIG. 17 is a perspective view of one embodiment of the shield body according to the system of the present invention.
Figure 18:
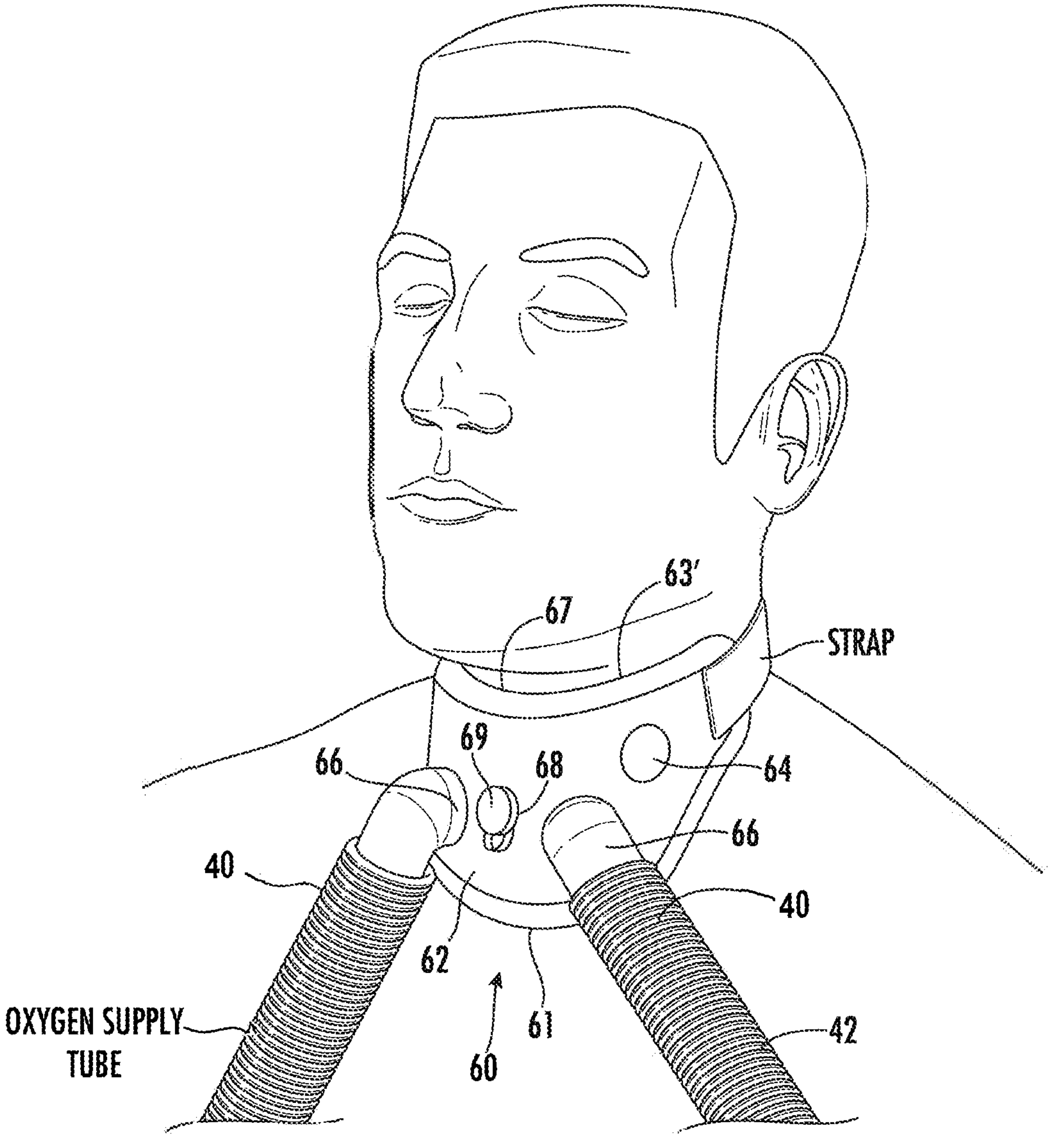
FIG. 18 is a perspective view of another embodiment of the shield body according to the system of the present invention.

With reference to at least FIGS. 16-18, in an alternative embodiment, the system 1' according to the present invention may be implemented with a trachea shield assembly 60 comprising a shield body 62 that is placed around the neck area of a patient to access the trachea. In such embodiments of the inventive system 1', it is contemplated that a trachea shield assembly 60 may be provided on order to perform an intubation or related procedure around the trachea area of the patient, e.g. a tracheostomy or a bronchoscopy. The trachea shield assembly 60 primarily comprises a shield body 62 a strap or other component used to retain the shield body 62 around the neck of the patient. As seen at least in FIGS. 17-18, the shield body 62 may comprise an upper end 67 and a lower end 61 designed to expand above and below an opening of the neck (shown in FIG. 16). The shield body 62 may comprise an opening 68, with an optional cap 69 or other sealing mechanism. The location of the opening 68 should correspond to the approximate location of the neck opening. As such, the opening 68 may permit insertion of intubation components directly to the trachea of the patient without requiring insertion through the mouth of the patient. It is contemplated that at least one vacuum opening 66 be provided on either side of the opening 68 to allow for other components to be attached to the shield body 62 around an outer surface thereof. An inner surface of the shield body 62 should be disposed against the neck area of the patient. Such other components that may be attached to the shield body 62 may comprise a vacuum tube 40, which may be connected around a connecting segment 16'. As shown in FIG. 18, an oxygen supply tube may also be connected to the connecting segment 16'. As such, the components connected through the openings 66, i.e., oxygen supply tube and/or vacuum tube, should be in disposed in fluid communication with an interior or inner surface of the shield body 62. Furthermore, a safety inhalation valve and/or a safety flutter valve 64 may also be disposed on the shield body 62 as an emergency feature in the event of patient asphyxiation or an oxygen feed failure or other failure.

Figure 14A:
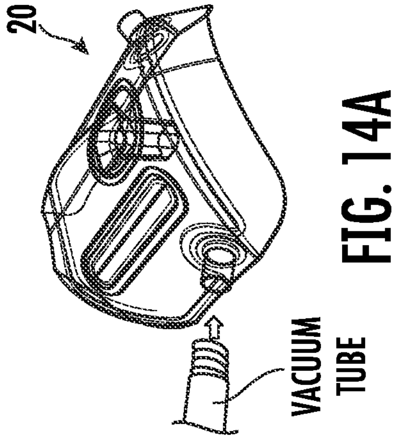
FIG. 14A is a perspective side view of one embodiment of the shield body of the system according to the present invention.
Figure 14B:
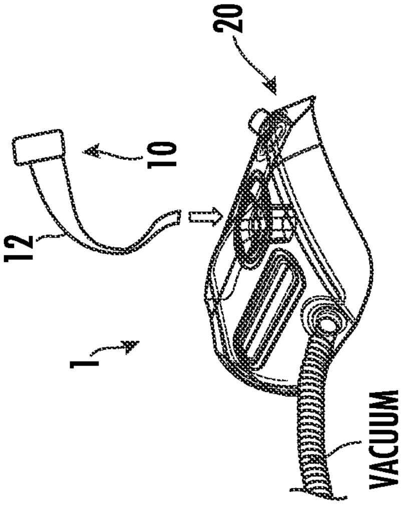
FIG. 14B is a perspective side view of one embodiment of the shield body, sleeve and vacuum tube of the system according to the present invention.
Figure 14C:
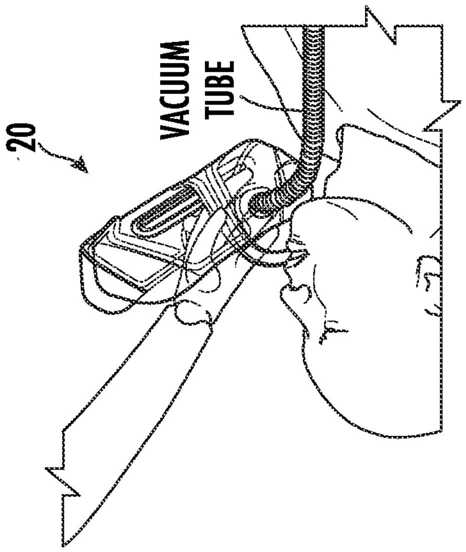
FIG. 14C is a perspective side view of another embodiment of the shield body, sleeve and vacuum tube according to the present invention.
Figure 14D:
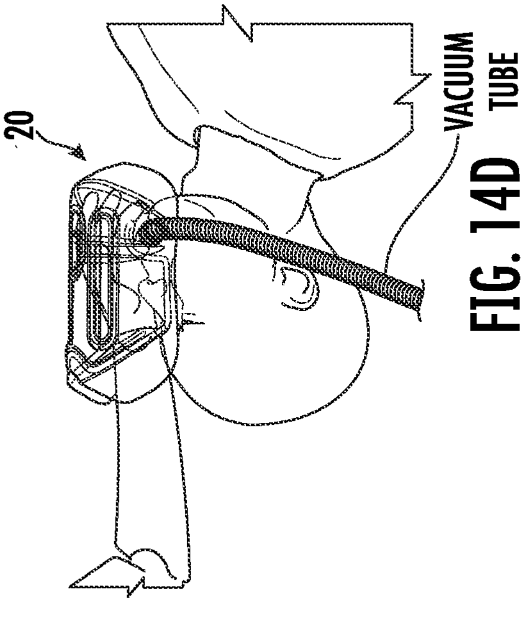
FIG. 14D is a perspective side view of yet another embodiment of the shield body, sleeve and vacuum tube according to the present invention.
Figure 14E:
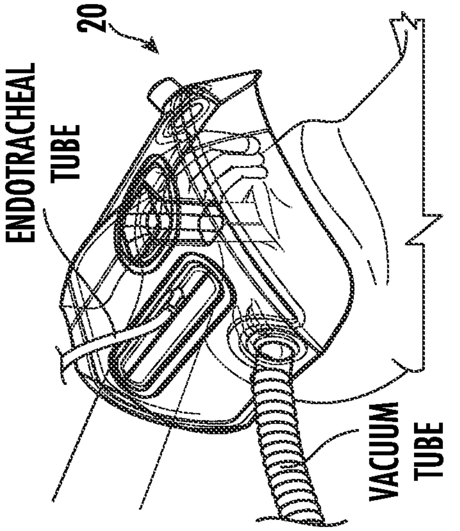
FIG. 14E is a perspective view of a further embodiment of the shield body, sleeve and vacuum tube according to the present invention.
Figure 14F:
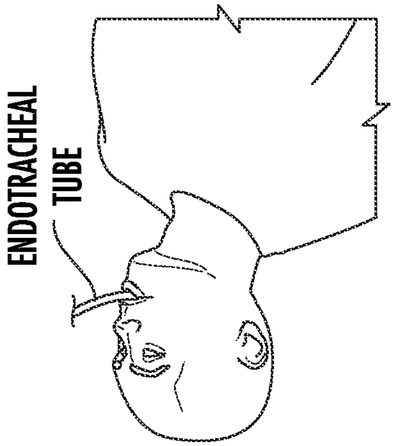
FIG. 14F is a perspective view of an intubated patient using the system according to the present invention.
Figure 15C:
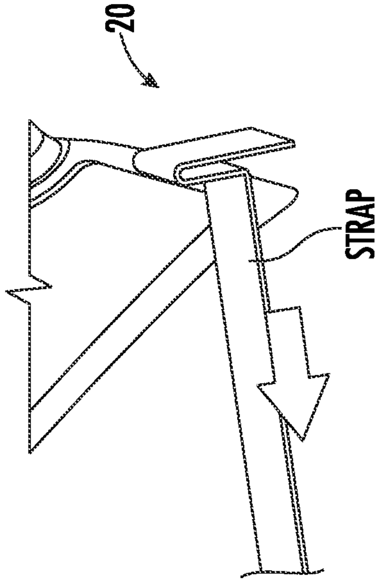
FIG. 15C is a perspective view of a portion of another embodiment of the system according to the present invention comprising a strap disposed on the shield body.
Figure 15B:
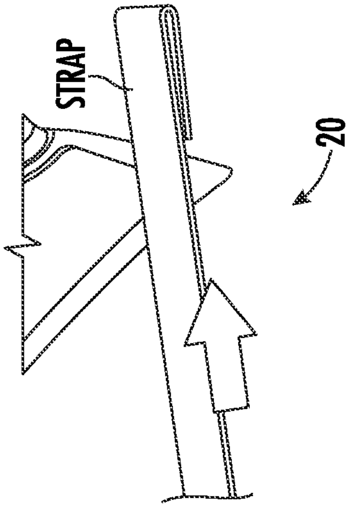
FIG. 15B is a perspective view of a portion of one embodiment of the system according to the present invention comprising a strap disposed on the shield body.
Figure 15A:
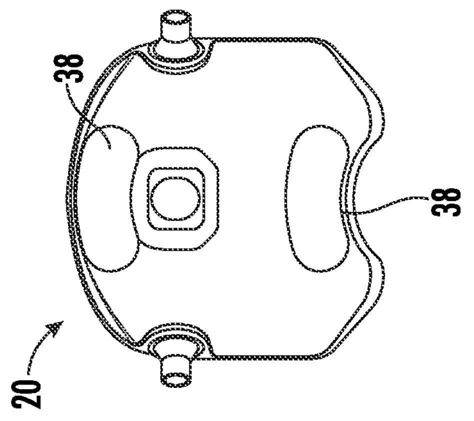
FIG. 15A is a top view of one embodiment of shield body of the system according to the present invention.
Figure 15E:
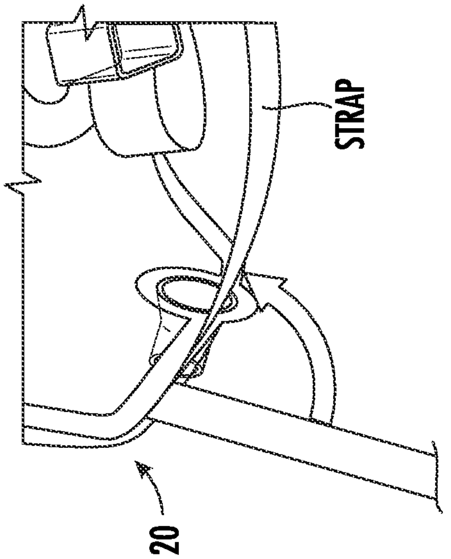
FIG. 15E is a perspective view of a portion of a further embodiment of the system according to the present invention comprising a strap disposed on the shield body.
Figure 15D:
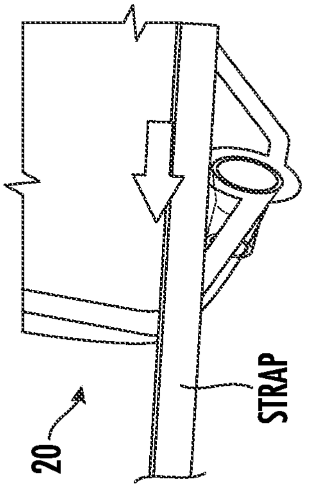
FIG. 15D is a perspective view of a portion of yet another embodiment of the system according to the present invention comprising a strap disposed on the shield body.
Figure 16B:
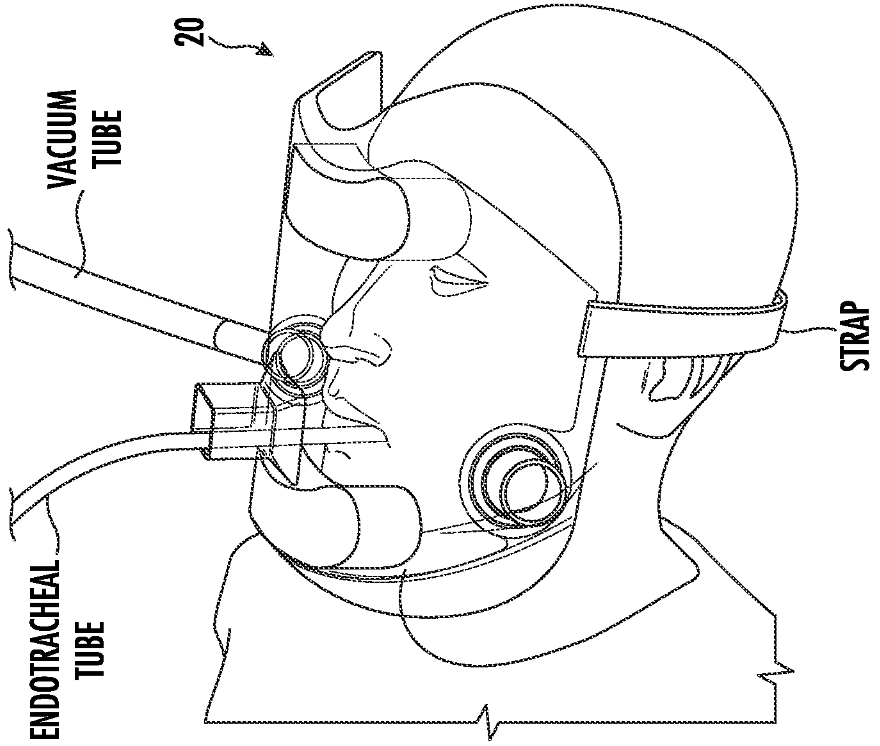
FIG. 16B is a perspective view of another embodiment of the shield body of the system according to the present invention disposed on the head of a patient.
Figure 19:
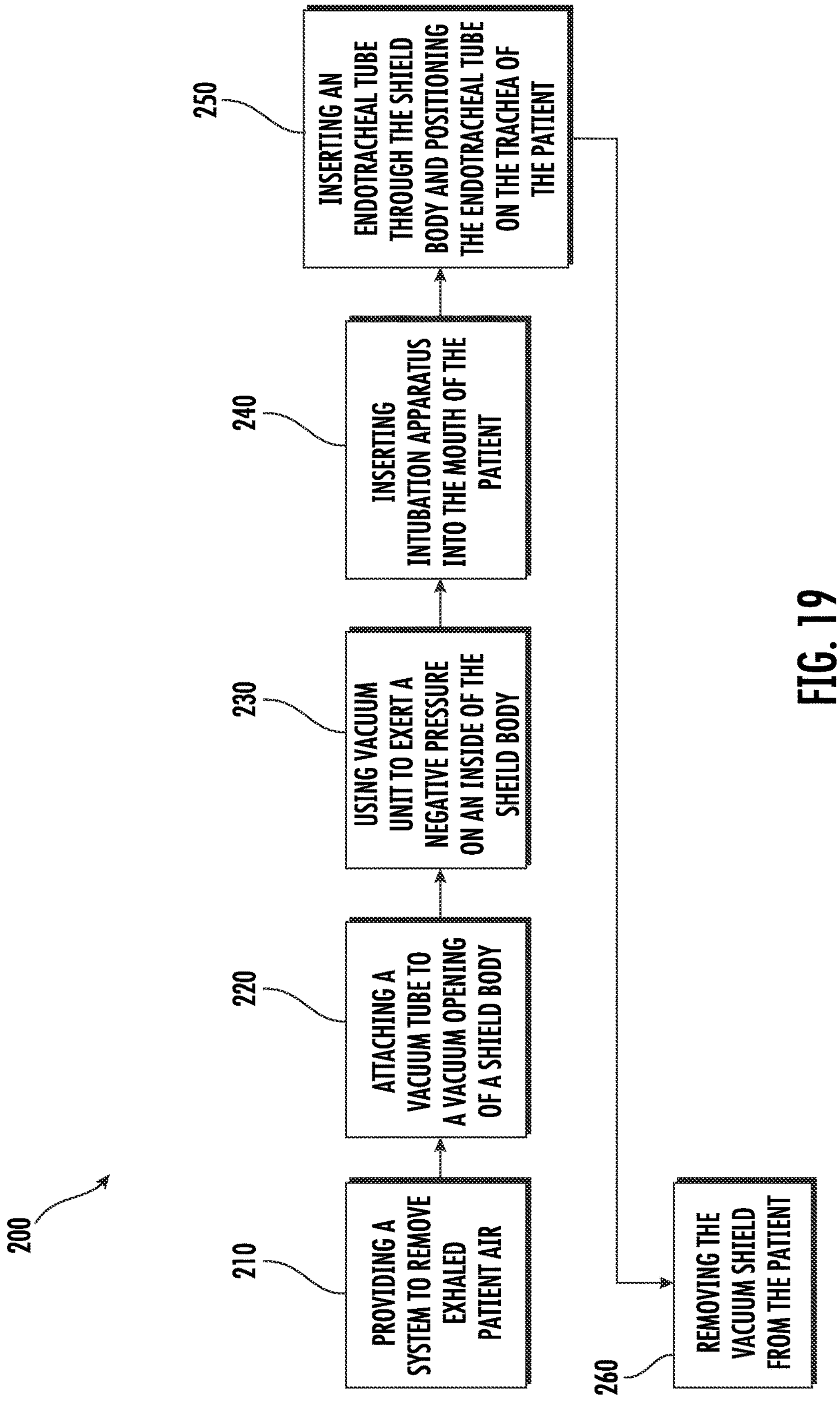
FIG. 19 is a diagrammatic representation of one embodiment of the method according to the present invention for removing exhaled air from a patient.

As described above, various components of the innovative system 1' may be disposed into an operative position as shown in at least FIGS. 14E and 16B. The shield body 24 and/or 62 may be connected to the vacuum tube and/or oxygen supply tube (e.g., FIG. 14A). Thereafter, a sleeve 12 or intubation apparatus may be inserted through opening 22 (e.g., FIG. 14B). Thereafter, the shield body 24 and/or 62 may be position on the patient (e.g., FIGS. 14C-14D). There after an endotracheal tube may be inserted through a slot 28 and/or opening 68 and into the mouth and/or trachea of the patient (e.g., FIG. 14E). Thereafter the shield body 24 may be removed once the patient is intubated (e.g., FIG. 14F). As shown in FIGS. 15A-16B and 17, in some embodiments the shield body 24 and/or 62 may be provided with a strap. As shown in FIGS. 15A-E, the strap may be inserted into a slot(s) of the shield body 24, which may be configured and dimensioned for insertion of the strap. Thereafter, the strap may adjusted to securely retain the shield body 24 onto the head of the patient. A leading end(s) of the strap, may be connected to other portions of the same strap, for example, with a hook and loop connection or other connection mechanism. With reference now to at least FIG. 19, the present invention is also directed towards a method 200 of removing exhaled air from a patient. As shown at 210, the method 200 comprises providing (i) providing a system 1' as defined herein configured to remove exhaled air from the patient wearing the medical mask. The system 1' may comprise: a vacuum unit 80, a vacuum tube 40; an air filter 70 operatively disposed on an inside of the vacuum tube 40; a vacuum shield assembly 20 comprising a shield body 24 that is configured and dimensioned for insertion of an intubation apparatus and at least one vacuum opening 26 disposed on the shield body 24; wherein the vacuum tube 40 is disposed in fluid communication with an inside of the shield body 24 and the vacuum unit 80, and wherein the vacuum tube 40, the shield body 24 and the vacuum unit 80 are collectively disposable into and out of an operative orientation and an inoperative orientation. The method 200 may further comprise: (ii) attaching the vacuum tube to the at least one vacuum opening, which is shown at 220; (iii) using the vacuum unit to exert a negative pressure on an inside of the shield body, which is shown at 230; (iv) inserting the intubation apparatus into the mouth of the patient, which is shown at 240; (v) inserting a endotracheal tube through the shield body and positioning the endotracheal tube on the trachea of the patient, which is shown at 250; and (vi) removing the shield body from the patient, which is shown at 260. The method 200 may further comprise inserting the intubation apparatus into the mouth of the patient when the shield body 24 is adjacently disposed to the face of the patient and using the vacuum unit 80 to exert a negative pressure on the enclosure area 34 or otherwise between the shield body 24 and the face of the patient.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A system configured to remove exhaled air from a patient, the system comprising:

a vacuum tube, a shield assembly structured for insertion of an intubation apparatus, said shield assembly comprising:

a shield body comprising an opening structured and dimensioned for insertion of the intubation apparatus, and at least one vacuum opening disposed on said shield body and structured for attachment to said vacuum tube, a vacuum unit, said vacuum unit disposed in fluid communication with an inside of said vacuum tube and an inside of said shield body, and said vacuum tube, said shield body and said vacuum unit collectively disposable into and out of an operative orientation and an inoperative orientation, wherein, in said inoperative orientation, the intubation apparatus is inserted through the shield body opening and the shield body is inclined away from a face of the patient, wherein, in said operative orientation, the intubation apparatus is inserted into the trachea of the patient in order to dispose said shield body adjacent to the face of the patient with an interior of said shield body facing the patient and defining an enclosure area between the shield body and the face of the patient, wherein the enclosure area between the shield body and the face of the patient is defined in response to the intubation apparatus being inserted into the trachea of the patient, and wherein said vacuum unit is activated in said operative orientation to exert a negative pressure through said vacuum tube on said enclosure area such that air is removed from the enclosure area through said vacuum tube.

2. The system as recited in claim 1 wherein said shield body is disposable into and out of an operative position and an inoperative position.

3. The system as recited in claim 2 wherein said operative position comprises the intubation apparatus disposed on said shield opening and into the mouth of the patient, and said interior of said shield body facing the patient.

4. The system as recited in claim 1 wherein said operative orientation comprises:

said shield body disposed into an operative position comprising the intubation apparatus disposed on said shield opening and in the mouth of the patient and said interior of said shield body facing the patient, and said vacuum unit activated and exerting the negative pressure on the inside of said shield body at least partially removing exhaled air from the patient, wherein said vacuum unit exerts said negative pressure while the intubation apparatus is inserted through said shield opening and into the mouth of the patient.

5. The system as recited in claim 1 wherein said shield body of said shield assembly comprises:

a top surface and a bottom surface, a top portion disposed on a distal end of said shield body, a first side segment and a second side segment, each one of said first side segment and said second side segment disposed on a proximal end of said shield body, and said top portion and said bottom surface of said shield body collectively define the enclosure area.

6. The system as recited in claim 5 wherein each of said first side segment and said second side segment are disposed in a spaced apart relation to one another; said first side segment and said second side segment collectively defining an aperture configured and dimensioned to allow access to a hand and arm of a user to said enclosure area.

7. The system as recited in claim 5 further comprising a reinforcement structure disposed around said proximal end of said shield body; said reinforcement structure configured to at least partially reduce bending of said shield body.

8. The system as recited in claim 5 further comprising an overlapping portion formed around said distal end of said shield body; said overlapping portion configured to at least partially reduce bending of said shield body.

9. The system as recited in claim 5 wherein said operative orientation comprises said vacuum unit activated and exerting a negative pressure around the enclosure area at least partially removing exhaled air from the patient between said shield body and the patient.

10. The system as recited in claim 5 further comprising at least one slot structured to allow an insertion of an endotracheal tube into said enclosure area.

11. A system configured to remove exhaled air from a patient, the system comprising:

a vacuum tube, an intubation apparatus assembly comprising a sleeve, said sleeve configured and dimensioned to receive an intubation apparatus on an inside thereof, said sleeve further configured and dimensioned for insertion into the mouth of the patient, a shield assembly structured for insertion of said sleeve, said shield assembly comprising:

a shield body comprising a top surface and a bottom surface, said shield body further comprising a flexible material, a top portion comprising a flexible material and disposed on a distal end of said shield body, a first side segment and a second side segment, each one of said first side segment and said second side segment disposed on a proximal end of said shield body, said top portion and said bottom surface of said shield body collectively defining an enclosure area, said shield body comprising an opening structured and dimensioned for insertion of the said sleeve, at least one vacuum opening disposed on said shield body and structured for attachment to the vacuum tube, and said shield body and said sleeve collectively disposable into and out of an operative position and an inoperative position, and a vacuum unit, wherein:

said vacuum tube, said shield body and said vacuum unit collectively disposable into and out of an operative orientation and an inoperative orientation, in said inoperative orientation, the intubation apparatus is inserted through the shield body opening and the shield body is inclined away from a face of the patient, in said operative orientation, the intubation apparatus is inserted into the trachea of the patient in order to dispose said shield body adjacent to the face of the patient, the enclosure area between the shield body and the face of the patient is defined in response to the intubation apparatus being inserted into the trachea of the patient, said operative orientation comprises said vacuum unit exerting a negative pressure within said enclosure area between said shield body and the patient to remove exhaled air from the patient.

12. The system as recited in claim 11 wherein said sleeve comprises a sleeve body configured and dimensioned to correspond to a sleeve body of the intubation apparatus; said intubation apparatus assembly comprising an audiovisual component.

13. The system as recited in claim 11 wherein said shield body comprises a sleeve retainer disposed on said bottom surface; said sleeve retainer configured and dimensioned to orient said sleeve into the mouth of the patient.

14. The system as recited in claim 11 wherein a sleeve retainer comprises at least one expandable component; said at least one expandable component defined along the length of said sleeve retainer and structured to at least partially allow for movement of said sleeve within said shield body.

15. A method for removing exhaled air from a patient, the method comprising:

(i) providing a system configured to remove exhaled air from the patient, the system comprising:

a vacuum tube, a shield assembly structured for insertion of an intubation apparatus, the shield assembly comprising:

a shield body comprising at least an opening structured and dimensioned for insertion of the intubation apparatus, and at least one vacuum opening disposed on the shield body and structured for attachment to the vacuum tube, and a vacuum unit, (ii) attaching the vacuum tube to the at least one vacuum opening, (iii) using the vacuum unit to exert a negative pressure on an inside of the shield body within an enclosure area defined between the shield body and the face of the patient, (iv) inserting the intubation apparatus into the at least one opening of the shield body in an inoperative orientation of the shield body when the shield body is inclined away from the face of the patient, (v) inserting the intubation apparatus into the mouth of the patient in an operative position of the shield body when the shield body is adjacent to the face of the patient, (vi) inserting an endotracheal tube through the shield body and positioning the endotracheal tube on the trachea of the patient in order to dispose the shield body adjacent to the face of the patient to define the enclosure area, and (vii) removing the vacuum shield from the patient.

16. The method as recited in claim 15 wherein (iv) inserting the intubation apparatus into the mouth of the patient in an operative position of the shield body when the shield body is adjacent to the face of the patient comprises: using the vacuum unit to exert a negative pressure between the shield body and the face of the patient.

* * * * *